Figure 1A:
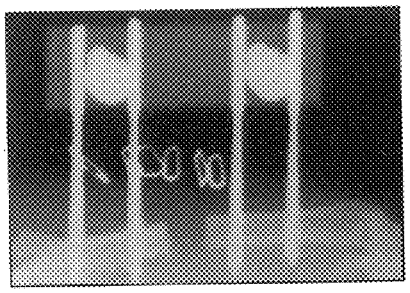

US005962427A

United States Patent [19]
Goldstein et al.

[11] Patent Number: 5,962,427
[45] Date of Patent: *Oct. 5, 1999

[54] IN VIVO GENE TRANSFER METHODS FOR WOUND HEALING

[75] Inventors: Steven A. Goldstein; Jeffrey Bonadio, both of Ann Arbor, Mich.

[73] Assignee: The Regent of the University of Michigan, Ann Arbor, Mich.

[ * ] Notice: This patent is subject to a terminal disclaimer.

[21] Appl. No.: 08/631,334

[22] Filed: Apr. 12, 1996

Related U.S. Application Data

[63] Continuation-in-part of application No. PCT/US95/02251, Feb. 21, 1995, which is a continuation-in-part of application No. 08/316,650, Sep. 30, 1994, which is a continuation-in-part of application No. 08/199,780, Feb. 18, 1994, Pat. No. 5,763,416.

[51] Int. Cl.$^6$ .................................................. A61K 48/00
[52] U.S. Cl. ......................... 514/44; 435/320.1; 435/325; 435/455; 435/458; 536/24.5; 424/93.21
[58] Field of Search ............................. 514/44; 424/85.1, 424/198.1, 426, 486, 93.21; 435/70.3, 244, 320.1, 240.2, 323, 455, 458; 530/389.2; 536/24.5; 935/52

[56] References Cited

U.S. PATENT DOCUMENTS

| | | | |
|---|---|---|---|
| 4,137,921 | 2/1979 | Okuzumi et al. | 128/335.5 |
| 4,166,800 | 9/1979 | Fong | 252/316 |
| 4,181,983 | 1/1980 | Kulkarni | 3/1 |
| 4,243,775 | 1/1981 | Rosensaft et al. | 525/415 |
| 4,279,249 | 7/1981 | Vert et al. | 128/92 D |
| 4,300,565 | 11/1981 | Rosensaft et al. | 128/335.5 |
| 4,347,234 | 8/1982 | Wahlig et al. | 424/15 |
| 4,384,975 | 5/1983 | Fong | 427/213.36 |
| 4,390,519 | 6/1983 | Sawyer | 424/28 |
| 4,409,332 | 10/1983 | Jefferies et al. | 435/188 |
| 4,455,256 | 6/1984 | Urist | 260/112 R |
| 4,472,840 | 9/1984 | Jefferies | 3/1.9 |
| 4,530,449 | 7/1985 | Tunc | 623/16 |
| 4,538,603 | 9/1985 | Pawelchak et al. | 128/156 |
| 4,539,981 | 9/1985 | Tunc | 128/92 B |
| 4,563,350 | 1/1986 | Nathan et al. | 424/95 |
| 4,563,489 | 1/1986 | Urist | 524/21 |
| 4,568,559 | 2/1986 | Nuwayser et al. | 427/3 |
| 4,578,384 | 3/1986 | Hollinger | 514/8 |
| 4,585,797 | 4/1986 | Cioca | 514/773 |
| 4,591,501 | 5/1986 | Cioca | 424/28 |
| 4,596,574 | 6/1986 | Urist | 623/16 |
| 4,619,989 | 10/1986 | Urist | 530/417 |
| 4,623,588 | 11/1986 | Nuwayser et al. | 428/402.24 |

(List continued on next page.)

FOREIGN PATENT DOCUMENTS

| | | |
|---|---|---|
| 635372 | 6/1991 | Australia . |
| 0 614 974 A2 | 9/1994 | European Pat. Off. . |
| 42 19 626 A1 | 12/1993 | Germany . |
| WO 90/03733 | 4/1990 | WIPO . |
| WO 90/11092 | 10/1990 | WIPO . |
| WO 90/14074 | 11/1990 | WIPO . |
| WO 91/17424 | 11/1991 | WIPO . |
| WO 92/05199 | 4/1992 | WIPO . |
| WO 92/06702 | 4/1992 | WIPO . |
| WO 92/07573 | 5/1992 | WIPO . |
| WO 93/05751 | 4/1993 | WIPO . |
| WO 93/09229 | 5/1993 | WIPO . |
| WO 93/14778 | 8/1993 | WIPO . |
| WO 93/15109 | 8/1993 | WIPO . |
| WO 93/16739 | 9/1993 | WIPO . |
| WO 94/01139 | 1/1994 | WIPO . |
| WO 94/20615 | 9/1994 | WIPO . |

OTHER PUBLICATIONS

Agarwala, Neena, et al., "Specific Binding of Parathyroid Hormone to Living Osteoclasts", *Journal of Bone and Mineral Research*, 7:531–539, 1992.
Bonadio et al., "Transgenic mouse model of the mild dominant form of osteogenesis imperfecta," *Proc. Natl. Acad. Sci. USA*, 87:7145–7149, 1990.
Davidson et al., "A model system for in vivo gene transfer into the central nervous system using an adenoviral vector," *Nature Genetics*, 3:219–223, 1993.
Falcone et al., "Macrophage and Foam Cell Release of Matrix–bound Growth Factors," *The Journal of Biological Chemistry*, 268(15) :11951–11958, 1993.
Flaumenhaft et al., "Role of the Latent TGF–β Binding Protein in the Activation of Latent TGF–β by Co–Cultures of Endothelial and Smooth Muscle Cells," *The Journal of Cell Biology*, 120(4) :995–1002, 1993.
Majmudar et al., "Bone Cell Culture in a Three–Dimensional Polymer Bead Stabilizes the Differentiated Phenotype and Provides Evidence That Osteoblastic Cells Synthesize Type III Collagen and Fibronectin," *Journal of Bone and Mineral Research*, 6(8) :869–881, 1991.
Miyazono et al., "Retention of the Transforming Growth Factor–β1 Precursor in the Golgi Complex in a Latent Endoglycosidase H–sensitive Form," *The Journal of Biological Chemistry*, 267(8) :5668–5675, 1992.
Pereira et al., "Genomic organization of the sequence coding for fibrillin, the defective gene product in Marfan syndrome," *Human Molecular Genetics*, 2(7) :961–968, 1993.
Seitz et al., "Effect of Transforming Growth Factor β on Parathyroid Hormone Receptor Binding and cAMP Formation in Rat Osteosarcoma Cells", *Journal of Bone and Mineral Research*, 7:541–546, 1992.

(List continued on next page.)

*Primary Examiner*—Bruce R. Campbell
*Assistant Examiner*—Dave Trong Nguyen
*Attorney, Agent, or Firm*—Pennie & Edmonds LLP

[57] ABSTRACT

The present invention relates to an in vivo method for specific targeting and transfer of DNA into mammalian repair cells. The transferred DNA may include any DNA encoding a therapeutic protein of interest. The invention is based on the discovery that mammalian repair cells proliferate and migrate into a wound site where they actively take up and express DNA. The invention further relates to pharmaceutical compositions that may be used in the practice of the invention to transfer the DNA of interest. Such compositions include any suitable matrix in combination with the DNA of interest.

14 Claims, 7 Drawing Sheets

U.S. PATENT DOCUMENTS

| | | | |
|---|---|---|---|
| 4,670,393 | 6/1987 | Seeburg | 435/240 |
| 4,703,108 | 10/1987 | Silver et al. | 530/356 |
| 4,711,783 | 12/1987 | Huc et al. | 424/460 |
| 4,741,337 | 5/1988 | Smith et al. | 128/334 R |
| 4,744,365 | 5/1988 | Kaplan et al. | 128/335.5 |
| 4,761,471 | 8/1988 | Urist | 530/350 |
| 4,776,890 | 10/1988 | Chu | 106/161 |
| 4,789,663 | 12/1988 | Wallace et al. | 514/21 |
| 4,789,732 | 12/1988 | Urist | 530/350 |
| 4,795,804 | 1/1989 | Urist | 530/350 |
| 4,798,786 | 1/1989 | Tice et al. | 435/177 |
| 4,806,523 | 2/1989 | Bentz et al. | 514/2 |
| 4,818,542 | 4/1989 | DeLuca et al. | 424/491 |
| 4,833,125 | 5/1989 | Neer et al. | 514/12 |
| 4,837,285 | 6/1989 | Berg et al. | 530/356 |
| 4,839,130 | 6/1989 | Kaplan et al. | 264/235 |
| 4,844,854 | 7/1989 | Kaplan et al. | 264/235 |
| 4,865,846 | 9/1989 | Kaufman | 424/428 |
| 4,877,864 | 10/1989 | Wang et al. | 530/324 |
| 4,882,150 | 11/1989 | Kaufman | 424/428 |
| 4,884,854 | 12/1989 | Kaplan et al. | 264/235 |
| 4,889,119 | 12/1989 | Jamiolkowski et al. | 606/220 |
| 4,898,186 | 2/1990 | Ikada et al. | 606/62 |
| 4,898,734 | 2/1990 | Mathiowitz et al. | 424/426 |
| 4,902,508 | 2/1990 | Badylak et al. | 424/95 |
| 4,916,193 | 4/1990 | Tang et al. | 525/413 |
| 4,938,763 | 7/1990 | Dunn et al. | 604/891.1 |
| 4,946,450 | 8/1990 | Erwin | 604/294 |
| 4,952,402 | 8/1990 | Sparks et al. | 424/419 |
| 4,956,178 | 9/1990 | Badylak et al. | 424/551 |
| 4,957,902 | 9/1990 | Grinnell | 514/17 |
| 4,961,707 | 10/1990 | Magnusson et al. | 433/215 |
| 4,968,590 | 11/1990 | Kuberasampath et al. | 530/326 |
| 4,975,526 | 12/1990 | Kuberasampath et al. | 530/350 |
| 4,975,527 | 12/1990 | Koezuka et al. | 530/356 |
| 4,988,358 | 1/1991 | Eppley et al. | 623/16 |
| 5,001,169 | 3/1991 | Nathan et al. | 523/113 |
| 5,004,602 | 4/1991 | Hutchinson | 424/78 |
| 5,007,939 | 4/1991 | Delcommune et al. | 623/66 |
| 5,011,691 | 4/1991 | Oppermann et al. | 424/423 |
| 5,011,692 | 4/1991 | Fujioka et al. | 424/426 |
| 5,013,649 | 5/1991 | Wang et al. | 435/69.1 |
| 5,035,893 | 7/1991 | Shioya et al. | 424/447 |
| 5,037,749 | 8/1991 | Findlay | 435/176 |
| 5,039,660 | 8/1991 | Leonard et al. | 514/8 |
| 5,051,272 | 9/1991 | Hermes et al. | 427/2 |
| 5,059,123 | 10/1991 | Jernberg | 433/215 |
| 5,077,049 | 12/1991 | Dunn et al. | 424/426 |
| 5,080,665 | 1/1992 | Jarrett et al. | 606/219 |
| 5,081,106 | 1/1992 | Bentley et al. | 514/5 |
| 5,084,051 | 1/1992 | Törmälä et al. | 606/77 |
| 5,103,840 | 4/1992 | Kavoussi | 128/899 |
| 5,106,626 | 4/1992 | Parsons et al. | 424/423 |
| 5,106,748 | 4/1992 | Wozney et al. | 435/252.3 |
| 5,108,753 | 4/1992 | Kuberasampath et al. | 424/422 |
| 5,108,755 | 4/1992 | Daniels et al. | 424/426 |
| 5,108,922 | 4/1992 | Wang et al. | 435/325 |
| 5,110,604 | 5/1992 | Chu et al. | 424/484 |
| 5,116,738 | 5/1992 | Wang et al. | 435/69.1 |
| 5,118,667 | 6/1992 | Adam et al. | 514/12 |
| 5,120,322 | 6/1992 | Davis et al. | 604/265 |
| 5,124,155 | 6/1992 | Reich | 424/428 |
| 5,128,136 | 7/1992 | Bentley et al. | 424/443 |
| 5,128,326 | 7/1992 | Balazs et al. | 514/54 |
| 5,133,755 | 7/1992 | Brekke | 623/16 |
| 5,137,669 | 8/1992 | Leonard et al. | 264/120 |
| 5,141,905 | 8/1992 | Rosen et al. | 435/69.1 |
| 5,143,730 | 9/1992 | Fues et al. | 424/426 |
| 5,162,114 | 11/1992 | Kuberasampath et al. | 424/423 |
| 5,162,430 | 11/1992 | Rhee et al. | 525/54.1 |
| 5,164,368 | 11/1992 | Recker | 514/12 |
| 5,166,058 | 11/1992 | Wang et al. | 435/69.1 |
| 5,168,050 | 12/1992 | Hammonds, Jr. et al. | 435/69.1 |
| 5,171,217 | 12/1992 | March et al. | 604/53 |
| 5,171,574 | 12/1992 | Kuberasampath et al. | 424/423 |
| 5,171,579 | 12/1992 | Ron et al. | 424/486 |
| 5,171,670 | 12/1992 | Kronenberg et al. | 435/68.1 |
| 5,182,365 | 1/1993 | Kuberasampath et al. | |
| 5,185,152 | 2/1993 | Peyman | 424/427 |
| 5,187,076 | 2/1993 | Wozney et al. | 435/69.1 |
| 5,192,741 | 3/1993 | Orsolini et al. | 514/4 |
| 5,196,185 | 3/1993 | Silver et al. | 424/45 |
| 5,197,977 | 3/1993 | Hoffman, Jr. et al. | 623/1 |
| 5,206,028 | 4/1993 | Li | 424/484 |
| 5,208,041 | 5/1993 | Sindrey | 424/562 |
| 5,208,219 | 5/1993 | Ogawa et al. | 514/12 |
| 5,223,263 | 6/1993 | Hostetler et al. | 424/450 |
| 5,227,157 | 7/1993 | McGinity et al. | 424/78.02 |
| 5,250,302 | 10/1993 | Oppermann et al. | 424/422 |
| 5,250,584 | 10/1993 | Ikada et al. | 523/114 |
| 5,258,494 | 11/1993 | Oppermann et al. | 530/326 |
| 5,263,985 | 11/1993 | Bao et al. | 623/16 |
| 5,264,618 | 11/1993 | Felgner et al. | 560/224 |
| 5,266,683 | 11/1993 | Oppermann et al. | 530/326 |
| 5,268,178 | 12/1993 | Calhoun et al. | 424/426 |
| 5,270,300 | 12/1993 | Hunziker | 514/12 |
| 5,271,961 | 12/1993 | Mathiowitz et al. | 427/213.31 |
| 5,273,964 | 12/1993 | Lemons | 514/2 |
| 5,275,826 | 1/1994 | Badylak et al. | 424/551 |
| 5,278,201 | 1/1994 | Dunn et al. | 523/113 |
| 5,278,202 | 1/1994 | Dunn et al. | 523/113 |
| 5,281,419 | 1/1994 | Tuan et al. | 424/426 |
| 5,281,422 | 1/1994 | Badylak et al. | 424/551 |
| 5,286,634 | 2/1994 | Stadler et al. | 435/172.3 |
| 5,288,496 | 2/1994 | Lewis | 424/426 |
| 5,292,802 | 3/1994 | Rhee et al. | 525/54.1 |
| 5,298,422 | 3/1994 | Schwartz et al. | 435/320.1 |
| 5,304,121 | 4/1994 | Sahatjian | 604/53 |
| 5,306,303 | 4/1994 | Lynch | 623/16 |
| 5,308,623 | 5/1994 | Fues et al. | 424/426 |
| 5,308,889 | 5/1994 | Rhee et al. | 523/113 |
| 5,317,010 | 5/1994 | Pang et al. | 514/12 |
| 5,320,624 | 6/1994 | Kaplan et al. | 606/77 |
| 5,324,307 | 6/1994 | Jarrett et al. | 606/219 |
| 5,324,519 | 6/1994 | Dunn et al. | 424/426 |
| 5,324,520 | 6/1994 | Dunn et al. | 424/435 |
| 5,324,775 | 6/1994 | Rhee et al. | 525/54.2 |
| 5,324,819 | 6/1994 | Oppermann et al. | 530/350 |
| 5,326,350 | 7/1994 | Li | 623/11 |
| 5,326,357 | 7/1994 | Kandel | 623/16 |
| 5,328,955 | 7/1994 | Rhee et al. | 525/54.1 |
| 5,344,654 | 9/1994 | Rueger et al. | 424/423 |
| 5,350,580 | 9/1994 | Muchow et al. | 424/437 |
| 5,352,463 | 10/1994 | Badylak et al. | 424/551 |
| 5,354,557 | 10/1994 | Oppermann et al. | 424/423 |
| 5,360,610 | 11/1994 | Tice et al. | 424/426 |
| 5,366,508 | 11/1994 | Brekke | 623/16 |
| 5,366,733 | 11/1994 | Brizzolara et al. | 424/426 |
| 5,366,734 | 11/1994 | Hutchinson | 424/426 |
| 5,366,875 | 11/1994 | Wozney et al. | 435/69.1 |
| 5,372,821 | 12/1994 | Badylak et al. | 424/551 |
| 5,445,833 | 8/1995 | Badylak et al. | 424/551 |
| 5,460,831 | 10/1995 | Kossovsky et al. | 424/493 |
| 5,464,650 | 11/1995 | Berg et al. | 427/2.3 |
| 5,470,829 | 11/1995 | Prisell et al. | 514/2 |
| 5,593,974 | 1/1997 | Rosenberg et al. | 514/44 |
| 5,674,703 | 10/1997 | Woo et al. | 435/69.1 |
| 5,698,531 | 12/1997 | Nabel et al. | 514/44 |
| 5,707,969 | 1/1998 | Nabel et al. | 514/44 |
| 5,723,119 | 3/1998 | Schwarz et al. | 424/85.2 |
| 5,770,580 | 6/1998 | Ledley et al. | 514/44 |

OTHER PUBLICATIONS

Alper, 1994, "Boning Up: Newly Isolated Proteins Heal Bad Breaks", Science 263:324–325.

Bandara, G. et al., 1992, "Gene Transfer to Synoviocytes: Prospects for Gene Treatment of Arthritis", DNA and Cell Biol. 11(3):227–231.

Beck, L.S. et al., 1991, "Rapid Publication of TGF–$\beta$1 Induces Bone Closure of Skull Defects", J. Bone Miner, Res. 6(11):1257–1265.

Boden, S.D. et al., 1989, "Estrogen Receptor mRNA Expression in Callus During Fracture Healing in the Rat", Calcif. Tissue Int. 45:324–325.

Bonnarens and Einhorn, 1984, "Production of a Standard Closed Fracture in Laboratory Animal Bone", J. Orthop. Res. 2:97–101.

Carrington, J.L. et al., 1988, "Accumulation, Localization and Compartmentalization of Transforming Growth Factor $\beta$ During Endochondral Bone Development", J. Cell. Biol. 107:1969–1975.

Centrella, M. et al., 1988, "Skeletal Tissue and Transforming Growth Factor $\beta$", FASEB J. 2:3066–3073.

Chen, T.L. et al., 1991, "Bone Morphogenetic Protein–2b Stimulation of Growth and Osteogenic Phenotypes in Rat Osteoblast–like Cells: Comparison with TGF–$\beta$1", J. Bone Miner. Res. 6(12):1387–1393.

Cunningham, N.S. et al., 1992, "Osteogenin and Recombinant Bone Morphogenetic Protein 2B are Chemotactic for Human Monocytes and Stimulate Transforming Growth Factor $\beta$1 mRNA Expression", *Proc. Natl. Acad. Sci. USA* 89:11740–11744.

Gunasekaran, S. et al., 1993, "Mineralized Collagen as a Substitute for Autograft Bone that can Deliver Bone Morphogenic Protein", The 19th Annual Meeting of the Society for Biomaterials, p. 253.

Gunasekaran, S., 1993, "Role of Mineralized Collagen as an Osteoconductive Biomaterial", The 19th Annual Meeting of the Society for Biomaterials, p. 161.

Gunasekaran, S. et al., "Mineralization of Collagen Without Nucleating Proteins", 11:30 AM, V7.5, p.426.

Horowitz, M.C. et al., 1989, "Functional and Molecular Changes in Colony Stimulating Factor Secretion by Osteoblasts", Connective Tissue Res. 20:159–168.

Huggins, C.B. et al., 1936, "Experiments on the Theory of Osteogenesis", Arch. Surg. 32(6):915–931.

Izumi, T. et al., 1992, "Transforming Growth Factor $\beta$1 Stimulates Type II Collagen Expression in Cultured Periosteum–Derived Cells", J. Bone Miner. Res. 7(1):115–121.

Jingushi, S. et al., 1992, "Genetic Expression of Extracellular Matrix Proteins Correlates with Histologic Changes During Fracture Repair", J. Bone Miner. Res. 7(9):1045–1055.

Jingushi, S. et al., 1990, "Acidic Fibroblast Growth Factor (aFGF) Injection Stimulates Cartilage Enlargement and Inhibits Cartilage Gene Expression in Rat Fracture Healing", J. Orthop. Res. 8:364–371.

Joyce, M.E. et al., 1991, "Role of Growth Factors in Fracture Healing", Clinical and Experimental Approaches to Dermal and Epidermal Repair: Normal and Chronic Wounds, Proceedings of the Third International Symposium on Tissue Repair, Miami, FL, Jan. 10–14, 1990, Wiley–Liss, NY, NY pp. 391–416.

Joyce, M.E. et al., 1990, "Transforming Growth Factor–$\beta$and the Initiation of Chondrogenesis and Osteogenesis in the Rat Femur", J. Cell Biol. 110:2195–2207.

Luyten, F.P. et al., 1989, "Purification and Partial Amino Acid Sequence of Osteogenin, a Protein Initiating Bone Differentiation", J. Biol. Chem. 264(23):13377–13380.

O'Malley, Jr. and Ledley, 1993, "Somatic Gene Therapy in Otolaryngology–Head and Neck Surgery" Arch. Otolaryngol. Head Neck Surg. 119:1191–1197.

Ozkaynak, E. et al., 1990, "Op–1 cDNA Encodes an Osteogenic Protein in the TFG–$\beta$ Family", EMBO J. 9(7):2085–2093.

Paralkar, V.M. et al., 1991, "Identification and Characterization of Cellular Binding Proteins (Receptors) for Recombinant Human Bone Morphogenetic Protein 2B, a Initiator of Bone Differentiation Cascade", Proc. Natl. Acad. Sci. USA 88:3397–3401.

Roessier, B.J. et al., 1993, "Adenoviral–Mediated Gene Transfer to Rabbit Synovium in Vivo", J. Clin. Invest. 92:1085–1092.

Rosen, V. et al., 1989, "Purification and Molecular Cloning of a Novel Group of BMPs and Localization of BMP mRNA in Developing Bone", Connect. Tissue Res. 20:313–319.

Sampath, T.K. et al., 1984, "In Vitro Transformation of Mesenchymal Cells Derived From Embryonic Muscle into Cartilage in Response to Extracellular Matrix Components of Bone", Proc. Natl. Acad. Sci. USA 81:3419–3423.

Sampath and Reddy, 1981, "Dissociative Extraction and Reconstitution of Extracellular Matrix Components Involved in Local Bone Differentiation", Proc. Natl. Acad Sci. USA 78(12):7599–7603.

Sandusky, Jr., G.E. et al., 1992, "Histologic Findings After In Vivo Placement of Small Intestine Submucosal Vascular Grafts and Saphenous Vein Grafts in the Carotid Artery in Dogs", Am. J. Pathol. 140(2):317–324.

Shimell, M. et al., 1991, "The Drosophila Dorsal–Ventral Patterning Gene tolloid is Related to Human Bone Morphogenetic Protein 1", Cell 67:469–481.

Srivastava, C.H. et al., 1989, "Construction of a Recombinant Human Parvovirus B19: Adenoassociated Virus 2 (AAV) DNA Inverted Terminal Repeats are Functional in an AAV–B19 Hybrid Virus", Proc. Natl. Sci. USA 86:8078–8082.

Ulmer, J.B. et al., 1993, "Heterologous Protection Against Influenza by Injection of DNA Encoding a Viral Protein", Science 259:1745–1749.

Urist, M.R. et al., 1983, "Bone Cell Differentiation Growth Factors", Science 220:680–686.

Urist, M.R., 1965, "Bone: Formation by Autoinduction", Science 150:893–899.

Wang, E.A. et al., 1990, "Recombinant Human Bone Morphogenetic Protein Induces Bone Formation", Proc. Natl. Acad. Sci. USA 87:2220–2224.

Wilson, J.M. et al., "Somatic Gene Transfer in the Development of an Animal Model for Primary Hyperparathyroidism", Endocrinology 130(5):2947–2954.

Wolff, J.A. et al., 1990, "Direct Gene Transfer into Mouse Muscle in Vivo"Science 247:1465–1468.

Wozney, J.M. et al., 1988, "Novel Regulators of Bone Formation: Molecular Clones and Activities" Science 242:1528–1534.

Yasko, A.W. et al., 1992, "The Healing of Segmental Bone Defects, Induced by Recombinant Human Bone Morphogenetic Protein (rhBMP–2)", J. Bone and Joint Surg. 74–A(5):659–670.

Agarwala, N. et al., 1992, Specific Binding of Parathyroid Hormone to Living Osteoclasts:. J. Bone Miner. Res. 7:531–539.

Bonadio et al., 1990, "Transgenic Mouse Model of the Mild Dominant Form of Osteogenesis Imperfecta", Proc. Natl. Acad. Sci. USA 87:7145–7149.

Davidson et al., 1993, "A Model System for in Vivo Gene Transfer into the Central Nervous System Using an Adenoviral Vector", Nature Genetics 3:219–223.

Falcone et al., 1993, "Macrophage and Foam Cell Release of Matrix–Bound Growth Factors", J. Biol. Chem. 268(15):11951–11958.

Flaumenhaft et al., 1993, "Role of the Latent TGF–β Binding Protein in the Activation of Latent TGF–β by Co–Cultures of Endothelial and Smooth Muscle Cells.", J. Cell Biol. 120(4):995–1002.

Majmudar et al., 1991, "Bone Cell Culture in a Three–Dimensional Polymer Bead Stabilizes the Differentiated Phenotype and Provides Evidence that Osteoblastic Cells Synthesize Type III Collagen and Fibronectin" J. Bone Miner. Res. 6(8):869–881.

Miyazono et al., 1992, "Retention of the Transforming Growth Factor–β1 Precursor in the Golgi Complex in a Latent Endoglycosidase H–Sensitive Form" J. Biol. Chem. 267(8):5668–5675.

Pereira et al., 1993, "Genomic Organization of the Sequence Coding for Fibrillin, the Defective Gene Product in Marfan Syndrome", Hum. Mol. Genet. 2(7):961–968.

Seitz et al., 1992, Effect of Transforming Growth Factor β on Parathyroid Hormone Receptor Binding and cAMP Formation in Rat Osteosarcoma Cells, J. Bone Miner. Res. 7:541–546.

Selander–Sunnerhagen et al., 1992, "How an Epidermal Growth Factor (EGF)–Like Domain Binds Calcium", J. Biol. Chem. 267(27):19642–19649.

Steiner et al., 1992, "The New Enzymology of Precursor Processing Endoproteases", J. Biol. Chem. 267(33):23435–23438.

Stratford–Perricaudet et al., 1992, "Widespread Long–Term Gene Transfer to Mouse Skeletal Muscles and Heart", J. Clin. Invest. 90:626–630.

Rosen and Thies, 1992, "The BMP Proteins in Bone Formation and Repair", Trends in Genetics 8(3):97–102.

International Search Report from WO95/22611.

Badylak et al., 1992, "Directed Connective Tissue Remodeling Upon a Biologic Collagen Substrate". J. Cell. Biochem. Suppl. 16F:124.

Benevisty and Reshef, 1986, "Direct Introduction of Genes into Rats and Expression of the Genes", Proc. Natl. Acad. Sci. USA 83:9551–9555.

Bonadio, J. and Goldstein, S., 1994, "Direct Gene Transfer into Skeletal Tissue in Vivo", Gene Therapy Meeting: Cold Spring Harbor, Conference Abstract, Sep. 21–25.

Edelman et al., 1995, "c–myc in Vasculoproliferative Disease" Circulation Res. 76(2):1.2–1.8.

Evans and Robbins, 1995, "Possible Orthopaedic Applications of Gene Therapy", J. Bone and Joint Surg. 77–A(7):1103–1114.

Indolfi et al., 1995, "Inhibition of Cellular ras Prevents Smooth Muscle Cell Proliferation After Vascular Injury in vivo", Nature Medicine 1(16):541–545.

Badylak, S., Bonadio, J and Voytik, S., Invention Disclosure entitled: "Small Intestinal Submucosa as Biomaterial to Promote Gene Transfer", Sep. 4, 1992.

Kaneda et al., 1989, "Increased Expression of DNA Cointroduced with Nuclear Protein in Adult Rat Liver", Science 243:375–378.

Mannino and Gould–Fogerite, 1988, "Liposome Mediated Gene Transfer"BioTechniques 6(7):682–690.

Mumper et al., 1995, "Interactive Polymeric Gene Delivery Systems for Enhanced Muscle Expression", Abstract, Amer. Assoc. of Pharmaceutical Science, Miami Beach, FL, Nov. 6–9, 1995.

Nicolau et al., 1983, "In Vivo Expression of Rat Insulin After Intravenous Administration of the Liposome–Entrapped Gene for Rat Insulin I"Proc. Natl. Acad. Sci USA 80:1068–1072.

Simons et al., 1992, "Antisense c–myb Oligonucleotides Inhibit Intimal Arterial Smooth Muscle Cell Accumulation in Vivo", Nature 359:67–70.

Sumner et al., 1995, "Enhancement of Bone Ingrowth by Transforming Growth Factor–β", J. Bone and Joint Surg. 77–A(8):1135–1147.

Wolfe et al., 1991, "Conditions Affecting Direct Gene Transfer into Rodent Muscle in Vivo", BioTechniques 11(4):474–485.

Wu and Wu, 1988, "Receptor–Mediated Gene Delivery and Expression in Vivo", J. Biol. Chem. 263(29):14621–14624.

Yin et al., 1994, "Molecular Cloning of a Novel Fibrillin–Like cDNA: Expression in Callus Tissue as Alternatively Spliced Transcripts", 40th Annual Meeting, Orthopaedic Research Society, Conference Abstract, Feb. 21–24, 1994.

Zhu et al., 1994, "Direct Gene Transfer into Regenerating Achilles' Tendon", 40th Annual Meeting, Orthopaedic Research Society, Conference Abstract, Feb. 21–24, 1994.

U.S. Patent Application Serial No. 08/176,565, filed Jan. 03, 1994, entitled "Fluidized Intestinal Submucosa and its Use as an Injectable Tissue Graft".

U.S. Patent Application Serial No. 08/343,204, filed Nov. 22, 1994, entitled "Fluidized Intestinal Submucosa and its Use as an Injectable Tissue Graft".

U.S. Patent Application Serial No. 08/390,700, filed Feb. 17, 1995, entitled "Compositions and Method for Production of Transformed Cells".

U.S. Patent Application Serial No. 08/386,432, filed Feb. 10, 1995, entitled "Bone Graft Composition".

U.S. Patent Application Serial No. 08/386,452, filed Feb. 10, 1995, entitled "Submucosa as a Growth Substrate for Cells".

Ledley, F.D., 1987, "Somatic gene Therapy for Human Disease: Background and Prospects. Part I", J. Pediatrics 110(1):1–8.

James Wilson et al., Endocrinology, vol. 30, 5:2947–2954.

Matthews et al (Experimental Hematology 21:697–702, 1993).

Rosen and Thies, "The BMP proteins in bone formation and repair," Trends in Genetics, 8(3) :97–102, Mar. 1992.

International Search Report dated Sep. 15, 1995.

Nicolau et al., "In vivo expression of rat insulin after intravenous administration of the liposome–entrapped gene for rat insulin I," Proc. Natl. Acad. Sci. USA, 80:1068–1072, Feb., 1983.

Simons et al., "Antisense c–myb oligonucleotides inhibit intimal arterial smooth muscle cell accumulation in vivo," Nature, 359:67–70, Sep., 1992.

Sumner et al., "Enhancement of Bone Ingrowth by Transforming Growth Factor–β," The Journal of Bone and Joint Surgery, 77–A(8):1135–1147, Aug., 1995.

Wolff et al., "Conditions Affecting Direct Gene Transfer into Rodent Muscle In Vivo," BioTechniques, 11(4): 474–485, 1991.

Wolff et al., "Expression of naked plasmids by cultured myotubes and entry of plasmids into T tubules and caveolae of mammalian skeletal muscle," *Journal of Cell Science,* 103:1249–1259, 1992.

Indolfi et al., "Inhibition of cellular ras prevents smooth muscle cell proliferation after vascular injury in vivo," *Nature Medicine,* 1(6):541–545, Jun., 1995.

Invention Disclosure entitled "Small Intestinal Submucosa as Biomaterial to Promote Gene Transfer," Stephen G. Badylak, Jeffrey Bonadio and Sherry L. Voytik, Sep. 4, 1992.

Kaneda et al., "Increased Expression of DNA Cointroduced with Nuclear Protein in Adult Rat Liver," *Science,* 243:375–378, Jan., 1989.

Mannino and Gould–Fogerite, "Liposome Mediated Gene Transfer," *BioTechniques,* 6(7):682–690, 1988.

Mumper et al., "Interactive Polymeric Gene Delivery Systems for Enhanced Muscle Expression," *Abstract,* American Assoc. of Pharmaceutical Science, Miami Beach, FL, Nov. 6–9, 1995.

Badylak et al., "Directed Connective Tissue Remodeling Upon a Biologic Collagen Substrate," *J. Cell Biochem. Supplement* 16F, p. 124, Apr. 3–16, 1992.

Benevisty and Reshef, "Direct introduction of genes into rats and expression of the genes," *Proc. Natl. Acad. Sci. USA,* 83:9551–9555, Dec, 1986.

Bonadio and Goldstein, "Direct Gene Transfer into Skeletal Tissues In Vivo,"Gene Therapy Meeting: Cold Spring Harbor, Conference Abstract, Sep. 21–25, 1994.

Edelman et al., "c–myc in Vasculoproliferative Disease," *Circulation Research,* 76(2):1.2–1.8, Feb., 1995.

Evans and Robbins, "Possible Orthopaedic Applications of Gene Therapy," *The Journal of Bone and Joint Surgery,* 77–A(7):1103–1114, Jul., 1995.

U.S. Patent Application Serial No. 08/386,432; filed Feb. 10, 1995; entitled "Bone Graft Composition".

U.S. Patent Application Serial No. 08/386,452; filed Feb. 10, 1995; entitled "Submucosa as a Growth Substrate for Cells.".

Wu and Wu, "Receptor–mediated Gene Delivery and Expression in Vivo," *The Journal of Biological Chemistry,* 263(29):14621–14624, 1988.

Yin et al., "Molecular Cloning of a Novel Fibrillin–Like cDNA: Expression in Callus Tissue as Alternatively Spliced Transcripts," 40th Annual Meeting, Orthopaedic Research Society, Conference Abstract, Feb. 21–24, 1994.

Zhu et al., "Direct Gene Transfer into Regenerating Achilles' Tendon," 40th Annual Meeting, Orthopaedic Research Society, Conference Abstract, Feb. 21–24, 1994.

U.S. Patent Application Serial No. 08/176,565; filed Jan. 03, 1994; entitled "Fluidized Intestinal Submucosa and its Use as an Injectable Tissue Graft".

U.S. Patent Application Serial No. 08/343,204; filed Nov. 22, 1994; entitled "Fluidized Intestinal Submucosa and its Use as an Injectable Tissue Graft".

U.S. Patent Application Serial No. 08/390,700; filed Feb. 17, 1995; entitled "Compositions and Method for Production of Transformed Cells".

Figure 1B:
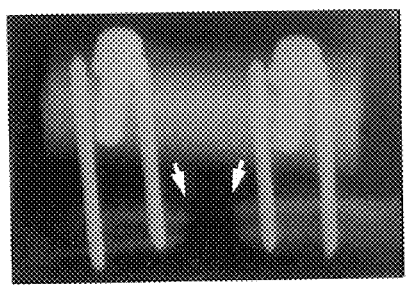
Figure 1C:
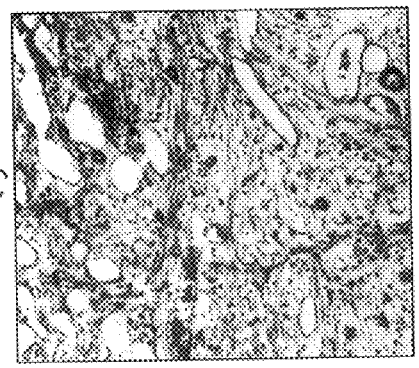
Figure 1D:
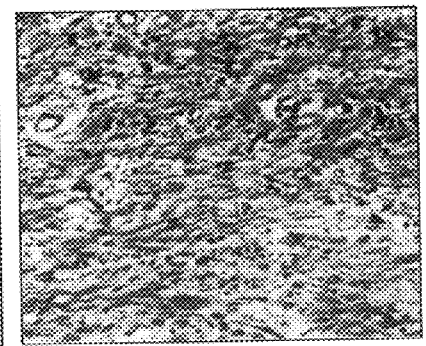
Figure 2:
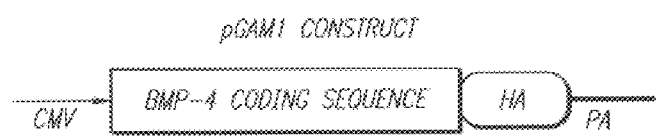

FIG. 3A1
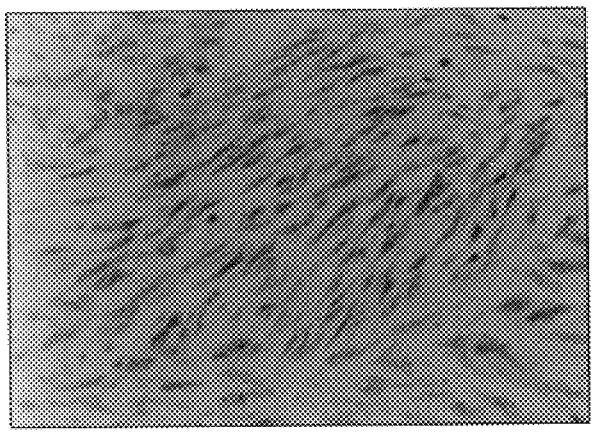
FIG. 3A2
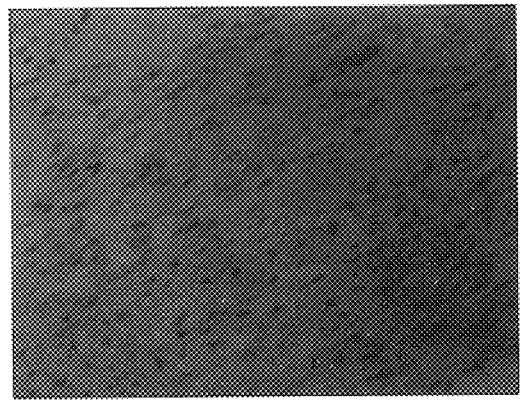
FIG. 3A3
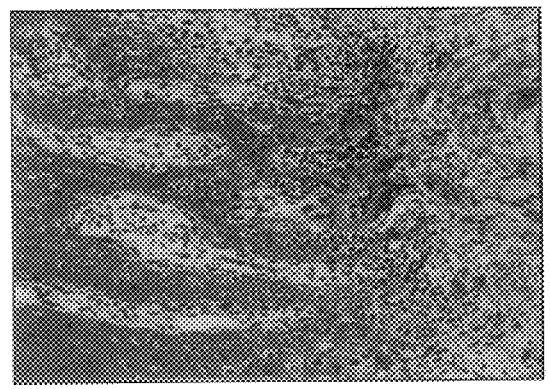

FIG. 3B1
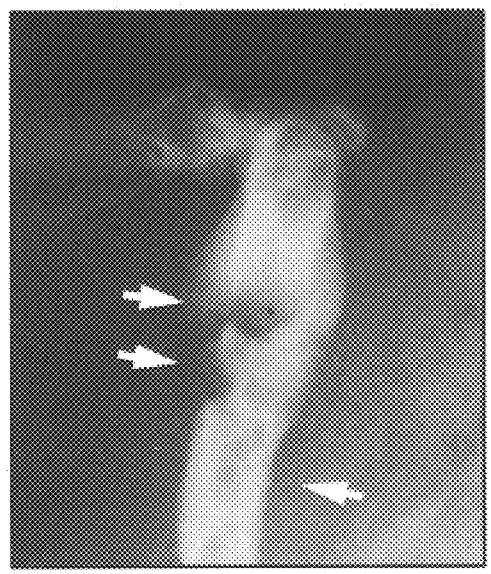
23 WEEKS POST-IMPLANTATION (PRE-MORTEM)
FIG. 3B2

FIG. 6A
FIG. 6B
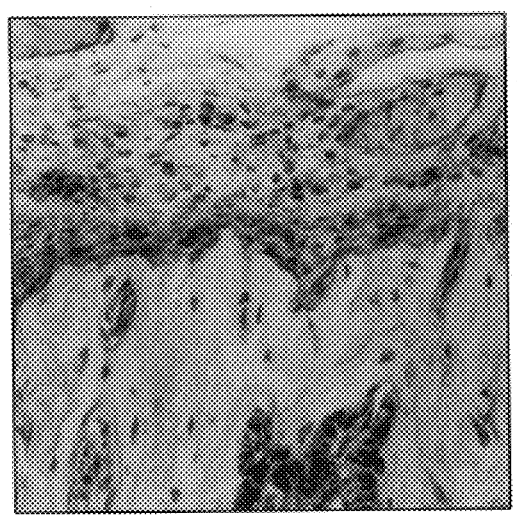
FIG. 6C
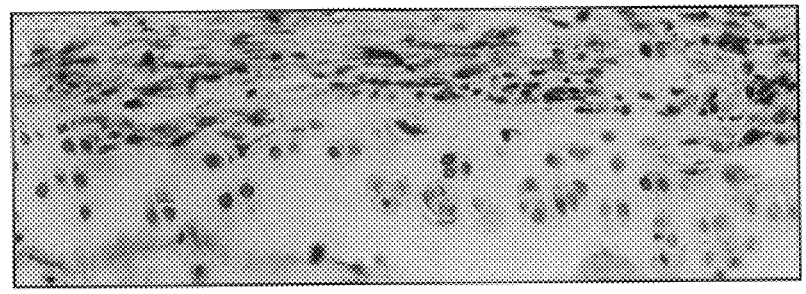

6 WEEKS

IN VIVO GENE TRANSFER METHODS FOR WOUND HEALING

This application is a Continuation-in-Part Application of PCT/US95/02251, filed Feb. 21, 1995 which is a Continuation-in-Part Application of U.S. Ser. No. 08/316,650, filed Sep. 30, 1994, which is a Continuation-in-Part Application of Ser. No. 08/199,780, filed Feb. 18, 1994.

TABLE OF CONTENTS

1. INTRODUCTION
2. BACKGROUND OF INVENTION
   2.1 WOUND HEALING
   2.2 GENE THERAPY
3. SUMMARY OF THE INVENTION
   3.1 DEFINITIONS
4. DESCRIPTION OF THE DRAWINGS
5. DETAILED DESCRIPTION OF THE INVENTION
   5.1 THE GENE ACTIVATED MATRIX
     5.1.1 THE MATRIX MATERIALS
     5.1.2 THE DNA
     5.1.3 PREPARATION OF THE GENE ACTIVATED MATRICES
   5.2. USES OF THE GENE ACTIVATED MATRIX
   5.3. BONE REGENERATION
   5.4. SOFT TISSUES
   5.5. ORGAN REGENERATION
   5.6. REGULATION OF ANGIOGENESIS
   5.7. REPAIR OF THE SKIN
6. EXAMPLE: IMPLANT MATERIAL FOR USE IN BONE GENE TRANSFER
7. EXAMPLE: IN VIVO PROTEIN DETECTION FOLLOWING TRANSGENE EXPRESSION
   7.1. β-GALACTOSIDASE TRANSGENE
   7.2. LUCIFERASE TRANSGENE
   7.3. PTH TRANSGENES
   7.4. BMP TRANSGENE
8. EXAMPLE: TRANSFER OF AN OSTEOTROPIC GENE STIMULATES BONE REGENERATION/REPAIR IN VIVO
9. EXAMPLE: DIRECT GENE TRANSFER INTO REGENERATING BONE IN VIVO
   9.1. MATERIALS AND METHODS
     9.1.1. MAMMALIAN HOST MODEL
     9.1.2. IMMUNOHISTOCHEMISTRY
     9.1.3. LUCIFERASE AND β-gal ENZYME ASSAYS
     9.1.4. pGAM1 EXPRESSION PLASMID
     9.1.5. pGAM2 EXPRESSION PLASMID
     9.1.6. PREPARATION OF GENE ACTIVATED COLLAGEN SPONGES
     9.1.7. RADIOGRAPHY
   9.2. RESULTS
     9.2.1. OSTEOTOMY MODEL
     9.2.2. MARKER GENE STUDIES
     9.2.3. BMP-4 GENE TRANSFER
     9.2.4. TRANSFER AND EXPRESSION OF A PLASMID COCKTAIL (BMP-4+PTH1-34)
10. EXAMPLE: TRANSFER OF GENES TO REGENERATING TENDON AND TO REGENERATING CRUCIATE LIGAMENT IN VIVO
    10.1. MATERIALS AND METHODS
    10.2. RESULTS
11. EXAMPLE: ADENOVIRAL GENE TRANSFER INTO REGENERATING BONE IN VIVO
    11.1. MATERIALS AND METHODS
    11.2. RESULTS
12. EXAMPLE: TRANSFER OF GENES TO SKELETAL MUSCLE
    12.1. MATERIALS AND METHODS
      12.1.1 PREPARATION OF DNA-PLGA COATING COMPOSITION
      12.1.2 COATING A SURGICAL SUTURE
      12.1.3 REPAIRING SKELETAL MUSCLE WITH THE COATED SUTURE
    12.2 RESULTS
13. EXAMPLE: TRANSFER OF GENES TO BLOOD VESSEL
    13.1. MATERIALS AND METHODS
    13.2. RESULTS

1. INTRODUCTION

The present invention relates to a novel in vivo method for the presentation and direct transfer of DNA encoding a therapeutic protein of interest into mammalian repair cells. The method involves implanting a matrix containing DNA of interest (referred to herein as a "gene activated matrix") into a fresh wound site. Repair cells, which normally originate in viable tissue surrounding the wound, proliferate and migrate into the gene activated matrix, wherein they encounter, take up and express the DNA. Transfected repair cells, therefore act, as in situ bioreactors (localized within the wound site) which produce agents (DNA-encoded RNAs, proteins, etc.) that heal the wound.

The invention further relates to pharmaceutical compositions that may be used in the practice of the invention to transfer the DNA of interest. Such compositions include any suitable matrix in combination with the DNA of interest.

2. BACKGROUND OF INVENTION

2.1 WOUND HEALING

Currently available wound healing therapies involve the administration of therapeutic proteins. Such therapeutic proteins may include regulatory factors involved in the normal healing process such as systemic hormones, cytokines, growth factors and other proteins that regulate proliferation and differentiation of cells. Growth factors, cytokines and hormones reported to have such wound healing capacity include, for example, the transforming growth factor-β superfamily (TGF-β) of proteins (Cox, D. A., 1995, Cell Biology International, 19:357–371) acidic fibroblast growth factor (FGF) (Slavin, J., 1995, Cell Biology International, 19:431–444), macrophage-colony stimulating factor (M-CSF) and calcium regulatory agents such as parathyroid hormone (PTH).

A number of problems are associated with the use of therapeutic proteins, i.e. cytokines, in wound healing therapies. First, the purification and/or recombinant production of therapeutic proteins is often an expensive and time-consuming process. Despite best efforts, however, purified protein preparations are often unstable making storage and use cumbersome, and protein instability can lead to unexpected inflammatory reactions (to protein breakdown products) that are toxic to the host.

Second, systemic delivery of therapeutic proteins, i.e. cytokines, can be associated with serious unwanted side effects in unwounded tissue. Due to inefficient delivery to specific cells and tissues in the body, administration of high doses of protein are required to ensure that sufficient amounts of the protein reach the appropriate tissue target. Because of the short half life in the body due to proteolytic degradation, the proteins must also be administered repeatedly which may give rise to an immune reaction to the therapeutic proteins. The circulation of high doses of therapeutic proteins is often toxic due to pleiotropic effects of the administered protein, and may give rise to serious side effects.

Third, exogenous delivery of recombinant proteins is inefficient. Attempts have been made to limit the administration of high levels of protein through immobilization of therapeutic protein at the target site. However, this therapeutic approach complicates the readministration of the protein for repeated dosing.

Fourth, for a variety of proteins such as membrane receptors, transcription factors and intracellular binding proteins, biological activity is dependant on correct expression and localization in the cell. For many proteins, correct cellular localization occurs as the protein is post-translationally modified inside the cells. Therefore, such proteins cannot be administered exogenously in such a way as to be taken up and properly localized inside the cell.

As these problems attest, current recombinant protein therapies for wound healing are flawed, because they do not present a rational method for delivery of exogenous proteins. These proteins, i.e. cytokines, are normally produced at their site of action in physiological amounts and efficiently delivered to cell surface signaling receptors.

2.2 GENE THERAPY

Gene therapy was originally conceived of as a specific gene replacement therapy for correction of heritable defects to deliver functionally active therapeutic genes into targeted cells. Initial efforts toward somatic gene therapy have relied on indirect means of introducing genes into tissues, called ex vivo gene therapy, e.g., target cells are removed from the body, transfected or infected with vectors carrying recombinant genes, and re-implanted into the body ("autologous cell transfer"). A variety of transfection techniques are currently available and used to transfer DNA in vitro into cells; including calcium phosphate-DNA precipitation, DEAE-Dextran transfection, electroporation, liposome mediated DNA transfer or transduction with recombinant viral vectors. Such ex vivo treatment protocols have been proposed to transfer DNA into a variety of different cell types including epithelial cells (U.S. Pat. No. 4,868,116; Morgan and Mulligan WO87/00201; Morgan et al., 1987, Science 237:1476–1479; Morgan and Mulligan, U.S. Pat. No. 4,980,286), endothelial cells (WO89/05345), hepatocytes (WO89/07136; Wolff et al., 1987, Proc. Natl. Acad. Sci. USA 84:3344–3348; Ledley et al., 1987 Proc. Natl. Acad. Sci. 84:5335–5339; Wilson and Mulligan, WO89/07136; Wilson et al., 1990, Proc. Natl. Acad. Sci. 87:8437–8441) fibroblasts (Palmer et al., 1987, Proc. Natl. Acad. Sci. USA 84:1055–1059; Anson et al., 1987, Mol. Biol. Med. 4:11–20; Rosenberg et al., 1988, Science 242:1575–1578; Naughton & Naughton, U.S. Pat. No. 4,963,489), lymphocytes (Anderson et al., U.S. Pat. No. 5,399,346; Blaese, R. M. et al., 1995, Science 270:475–480) and hematopoietic stem cells (Lim, B. et al. 1989, Proc. Natl. Acad. Sci. USA 86:8892–8896; Anderson et al., U.S. Pat. No. 5,399,346).

Direct in vivo gene transfer has recently been attempted with formulations of DNA trapped in liposomes (Ledley et al., 1987, J. Pediatrics 110:1); or in proteoliposomes that contain viral envelope receptor proteins (Nicolau et al., 1983, Proc. Natl. Acad. Sci. U.S.A. 80:1068); and DNA coupled to a polylysine-glycoprotein carrier complex. In addition, "gene guns" have been used for gene delivery into cells (Australian Patent No. 9068389). It has even been speculated that naked DNA, or DNA associated with liposomes, can be formulated in liquid carrier solutions for injection into interstitial spaces for transfer of DNA into cells (Felgner, WO90/11092).

Perhaps one of the greatest problems associated with currently devised gene therapies, whether ex vivo or in vivo, is the inability to transfer DNA efficiently into a targeted cell population and to achieve high level expression of the gene product in vivo. Viral vectors are regarded as the most efficient system, and recombinant replication-defective viral vectors have been used to transduce (i.e., infect) cells both ex vivo and in vivo. Such vectors have included retroviral, adenovirus and adeno-associated and herpes viral vectors. While highly efficient at gene transfer, the major disadvantages associated with the use of viral vectors include the inability of many viral vectors to infect non-dividing cells; problems associated with insertional mutagenesis; inflammatory reactions to the virus and potential helper virus production, and/or production and transmission of harmful virus to other human patients.

In addition to the low efficiency of most cell types to take up and express foreign DNA, many targeted cell populations are found in such low numbers in the body that the efficiency of presentation of DNA to the specific targeted cell types is even further diminished. At present, no protocol or method, currently exists to increase the efficiency with which DNA is targeted to the targeted cell population.

3. SUMMARY OF THE INVENTION

The present invention relates to a novel method for specific targeting and transfer of DNA into mammalian repair cells involved in wound healing in order to express therapeutic products at the wound site. The method of the invention involves administering a gene activated matrix into a fresh wound site in the body. In this setting, repair cells are localized to the wound site, where they become transfected and eventually produce DNA-encoded agents (RNAs, proteins, etc.) that enhance wound healing.

The invention is based, in part, on the discovery that repair cells, active in the wound healing process, proliferate and migrate from surrounding tissue into the area of the wound and infiltrate the gene activated matrix. The matrix acts as a scaffolding that promotes cell ingrowth, and, in turn, gene transfer, through the local accumulation of repair cells near the DNA. While in the matrix, repair cells are surprisingly efficient at taking up the DNA and expressing it as translational products, i.e., proteins, or transcriptional products, i.e., antisense and ribozymes. The transfected repair cells then serve as local bioreactors amplifying the production of the gene product in vivo.

While any number of DNA sequences can be used in the method, preferred DNA sequences are those that encode translational products (i.e. proteins) or transcriptional products (i.e. antisense or ribozymes) that (a) promote tissue repair; or (b) are capable of disrupting a disease process (thereby allowing normal tissue healing to take place).

The invention overcomes the shortcomings of procedures currently used for wound healing involving the administration of therapeutic proteins. First, DNA, which is both stable and non-toxic, can be safely administered in high doses in vivo. Second, repeated administration, while possible, is not required. The cells which take up and express the DNA provide a supply of gene product at the site of the wound. Third, the invention could be practiced in a way that addresses the temporal requirements of dosing. For example, the DNA can be presented in vectors that integrate into the genome of the targeted cell. In this case, all daughter cells will contain and express the transferred DNA thereby acting as a continuous source for the therapeutic agent. In contrast, non-integrating systems may be utilized wherein the DNA does not integrate into the genome and the gene is not passed on to daughter cells. In such an instance, when the wound healing process is completed and the gene product is no longer needed, the gene product will not be expressed.

The invention is demonstrated by way of examples, which show that genes can be reproducibly transferred and expressed in a variety of wounded soft and hard tissues in vivo. Specifically, it is shown that the method of the invention overcomes the problems associated with currently available gene therapy protocols. The method of the invention provides gene transfer to a suitable number of repair cells to achieve functional effects, i.e., in the absence of any further targeting or cellular identification by the practitioner. In vivo methods of gene therapy require some form of targeting which very often does not work. In the method of the invention, targeting is not a problem. By analogy, the DNA acts much like "bait" in a "trap": the DNA is encountered by unwitting repair cells that have proliferated and then migrated into the gene activated matrix. These cells, in turn, are surprisingly capable of taking up DNA and expressing it as a therapeutic agent.

In one embodiment of the invention, the method of the invention may be used as a drug delivery system through transfer of DNA into mammalian repair cells for the purpose of stimulating soft and hard tissue repair and tissue regeneration. The repair cells will be those cells that normally arrive at the area of the wound to be treated. Accordingly, there is no difficulty associated with the obtaining of suitable target cells to which the present therapeutic compositions should be applied. All that is required is the implantation of a gene activated matrix at the wound site. The nature of this biological environment is such that the appropriate repair cells will actively take up and express the "bait" DNA in the absence of any further targeting or cellular identification by the practitioner.

In another embodiment, the method of the invention, using both biological and synthetic matrices, may be used to transfer DNA into mammalian repair cells to stimulate skeletal regeneration. In a further embodiment, the method of the invention, using both biological and synthetic matrices, may be used to transfer DNA into mammalian cells to stimulate ligament and tendon repair. The method of the invention may further be employed, using both biological and synthetic matrices to transfer DNA into mammalian repair cells to stimulate skeletal muscle repair and/or blood vessel repair.

The DNA to be used in the practice of the invention may include any DNA encoding translational products (i.e. proteins) or transcriptional products (i.e. antisense or ribozymes) that promote tissue repair or are capable of disrupting a disease process. For example, the DNA may comprise genes encoding therapeutically useful proteins such as growth factors, cytokines, hormones, etc. Additionally, the DNA may encode anti-sense or ribozyme molecules that may inhibit the translation of mRNAs encoding proteins that inhibit wound healing or which induce inflammation.

The DNA encoding the therapeutic product of interest is associated with, or impregnated within, a matrix to form a gene activated matrix. Once prepared, the gene activated matrix is placed within the mammal at the site of a wound.

The invention is demonstrated by way of examples, wherein the efficient in vivo transfer and expression of genes into tissue undergoing repair and regeneration is demonstrated.

3.1 DEFINITIONS

As used herein, the following terms will have the meanings indicated below.

A gene activated matrix (GAM) is defined herein as any matrix material containing DNA encoding a therapeutic agent of interest. For example, gene activated matrices are placed within wound sites in the body of a mammalian host to enhance wound healing.

A repair cell is defined herein as any cell which is stimulated to migrate and proliferate in response to tissue injury. Repair cells are a component of the wound healing response. Such cells include fibroblasts, capillary endothelial cells, capillary pericytes, mononuclear inflammatory cells, segmented inflammatory cells and granulation tissue cells.

A wound site is defined as any location in the host that arises from traumatic tissue injury, or alternatively, from tissue damage either induced by, or resulting from, surgical procedures.

4. DESCRIPTION OF THE DRAWINGS

FIG. 1A. Femoral Osteotomy Model of Fibrous Nonunion. A 5 mm osteotomy was created surgically in the femurs of adult retired male breeder Sprague-Dawley rats. Gaps shown here are representative of the entire control group, with mammalian hosts receiving either an osteotomy alone (n=3), an osteotomy plus a collagen sponge (n=10) or an osteotomy plus a collagen sponge containing a control (marker gene) plasmid DNA (n=23). A plain x-ray film showing a control rat femur immediately after surgery. The gap was stabilized by an external fixator consisting of a plate and 4 pins. The skin incision was closed by metal clips.

FIG. 1B A plain x-ray film showing a control rat femur osteotomy 9 weeks after surgery. Rounded surgical margins (arrows) are due to a reactive bone formation and are consistent with the classical radiographic appearance of nonunion fracture.

FIG. 1C. Histology section of gap tissue 3 weeks post-surgery showing proliferating repair fibroblasts and capillaries embedded in an edematous extracellular matrix. Also present is a focal inflammatory infiltrate consisting of lymphocytes and macrophages.

FIG. 1D. Histology section from a 9 week control gap showing dense fibrous tissue. 1 cm=20 $\mu$m (C and D).

FIG. 2. Schematic diagram of the pGAM1 construct encoding mouse BMP-4. The position of the CMV promoter, BMP-4 coding sequence, HA epitope, and bovine growth hormone polyadenylation signal are shown.

FIG. 3A. BMP-4 expression by repair fibroblasts. Plasmid-encoded BMP-4 expression was detected in Bouins-fixed, demineralized, paraffin-embedded tissue sections using the anti-HA antibody and immunoperoxide method 4 weeks post-implantation of a gene activated matrix containing pGAM1 plasmid DNA. Arrows point to examples of positive (red-brown) staining of fibroblast cytoplasm (micrograph on upper left). These cells were identified as fibroblasts based on spindled morphology, growth in fascicle, and positive immunostaining for type I procollagen (not shown). Serial sections incubated with rabbit preimmune serum or without the first antibody were negative. Negative results were also obtained with sham-operated controls (collagen sponge alone) incubated with the anti-HA.11 antibody (micrograph on upper right). False positive staining of macrophages, osteoclasts, and osteoblasts was consistently observed in control sections incubated with the HA.11 antibody. An island of newly formed bone 3 weeks following pGAM1 transfer is shown in the micrograph at bottom. New bone is associated with formation of granulation tissue. Gap tissues were stained using Hematoxylin and eosin (upper micrographs) or with Gomori trichrome method (collagen-rich tissues appear green, lower micrographs). 1 cm=20 mm (upper micrograph).

FIG. 3B. The animal shown in FIG. 3A at 23 weeks post-operation. The ability of the animal to freely ambulate 5 weeks after removal of the external fixator is shown in the external view (top). The healed osteotomy site is visible. In the plain film radiograph (bottom), the arrow indicates the approximate position of the osteotomy gap, which is filled with radio-dense tissue. Note that the external fixator has been removed. As indicated by the variegated pattern, bone remodeling is taking place. Arrowheads point to defects in bone adjacent to the gap (a consequence of pin placement). The two distal pin sites were completely healed at this time (not shown).

Figure 4A:
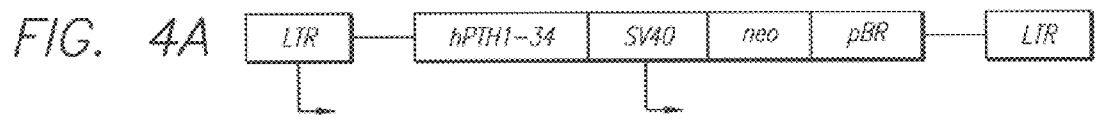

FIG. 4A. Schematic diagram of the pGAM2 construct encoding human PTH1-34. The position of an upstream long terminal repeat that drives PTH1-34 expression (arrow), the PTH1-34 coding sequence, the SV40 promoter that drives neo expression (arrow), the neo coding sequence, pBR sequences, and the downstream long terminal repeat are shown.

Figure 4B:
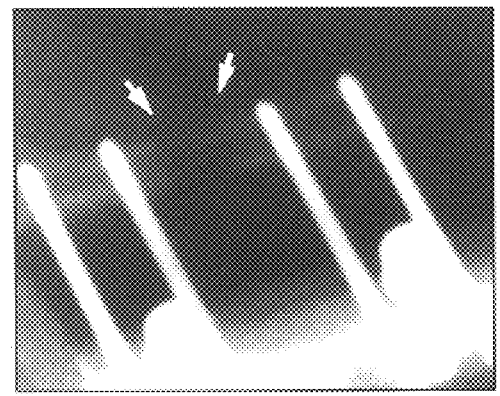

FIG. 4B. PTH1-34 gene transfer and expression drives new bone formation in vivo. Plain film radiograph showing new bone bridging of a 5 mm osteotomy gap 9 weeks post-implantation in an animal that received a gene activated matrix containing pGAM2 plasmid DNA. Arrows point to radio-dense tissue in the gap. Results shown here are representative of experiments with one additional animal.

Figure 5A:
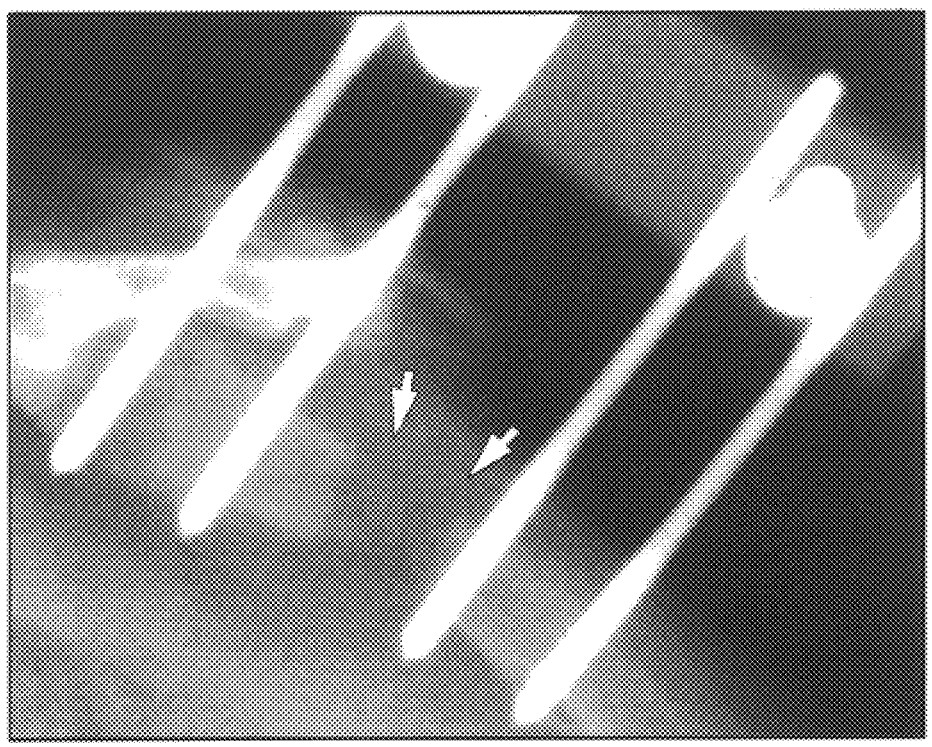
Figure 5B:
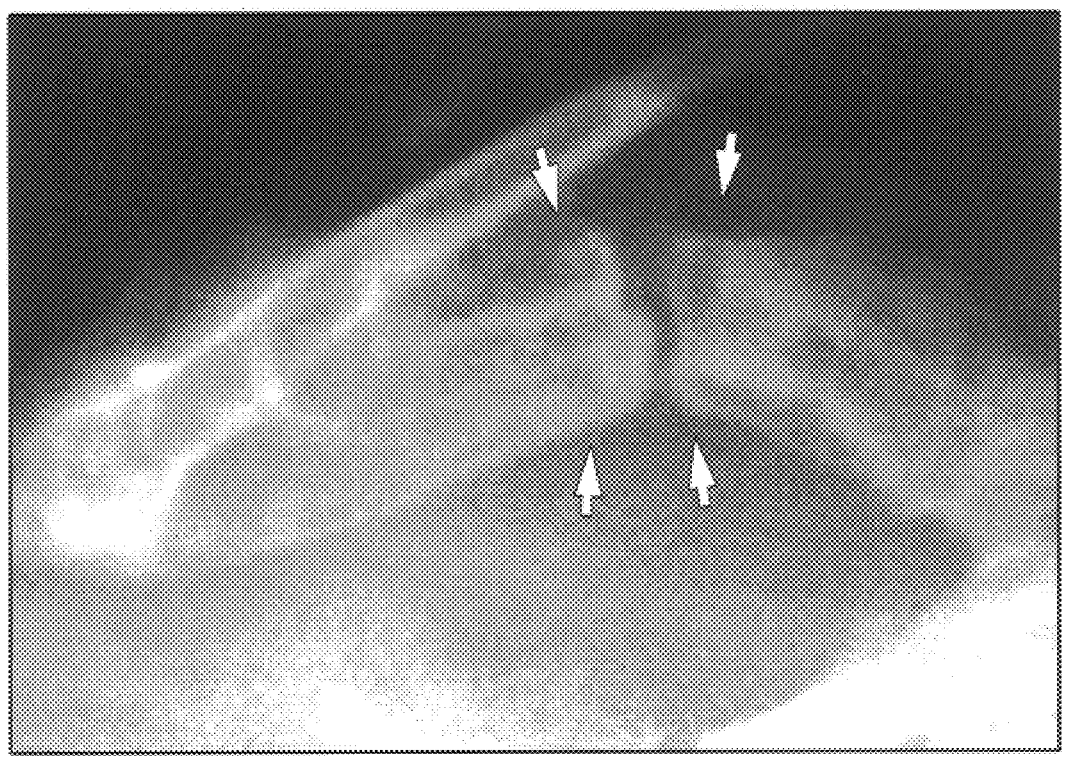

FIG. 5. New bone formation in vivo via a two-plasmid GAM. (top) Plain film radiograph showing new bone bridging of a 5 mm gap 4 weeks post-implantation in an animal that received a gene activated matrix containing pGAM1 plus pGAM2 plasmid DNA. Arrows point to radio-dense tissue in the gap (confirmed histologically to be bone). (bottom) Plain film radiograph of the gap shown in photo at top following removal (5 weeks earlier; total of 17 weeks post-surgery) of the external fixator. Arrows indicate location of the gap, which is filled with radio-dense tissue except for a strip of undermineralized tissue near the proximal surgical margin. As indicated by the variegated pattern, an extensive remodeling response is taking place. Results shown here are representative of experiments with one additional animal.

FIG. 6. Adenovirus-mediated Gene Transfer into Bone Repair/Regeneration Cells in vivo. The UltraFiber™ implant was soaked for 6 min. in a solution of the AdCMVlacZ virus ($10^{10}$–$10^{11}$ plaque forming units or PFU/ml) and then implanted into the osteotomy site. The defect was allowed to heal for 3 weeks, during which time the progress of the wound healing response was monitored by weekly radiographic examination. By three weeks, it was estimated that 40% of the defect was filled with callus tissue. The mammalian host was sacrificed and tissues were fixed in Bouins fixation and then demineralized for 7 days using standard formic acid solutions. Photomicrographs were taken from transverse sections of new bone (callus) that formed in the osteotomy site 3 weeks after surgery. Panel at top left: Note the positive (red) β-gal cytoplasmic staining of callus tissue cells from the UltraFiber™ adenovirus implant. This result indicates that cell surface receptors that mediate infection, and thus viral transduction, are expressed by (at least one population) callus cells during the fracture healing process. Panel at top right: serial section negative control stained with the vehicle of the β-gal antibody plus cocktail of non-specific rabbit LgG antibodies. Panel at bottom: note the positive (red) β-gal nuclear staining of chondrocytes in the osteotomy site filled with UltraFiber™ and AdRSVnt-lacZ. This result demonstrates the exquisite specificity of the anti-β-gal antibody, and conclusively demonstrates expression of the marker gene product in the osteotomy gap.

Figure 7:
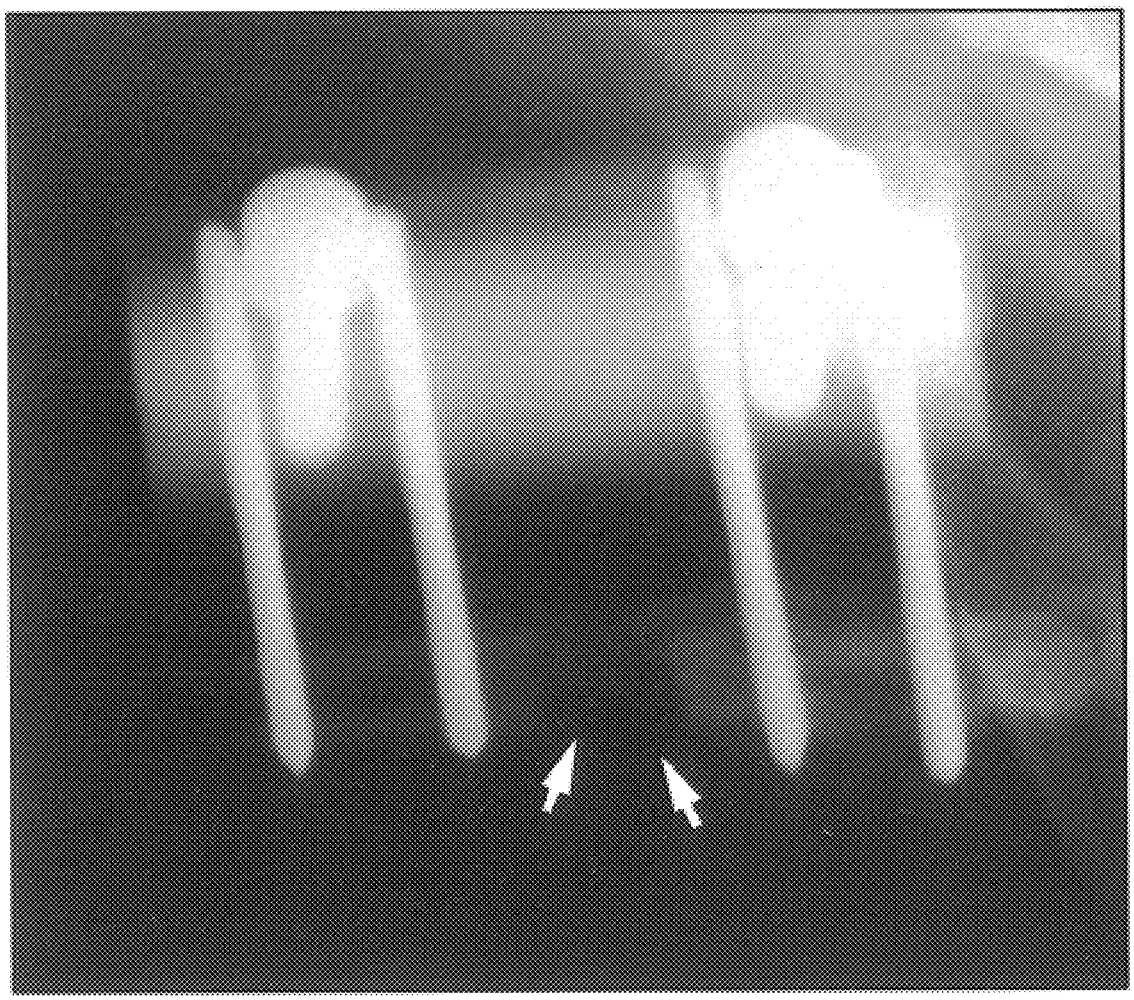

FIG. 7. pGAM2 plasmid gene transfer to repair fibroblasts results in new bone growth in the rat osteotomy model. Plain film radiograph showing new bone bridging of a 5 mm gap 6 weeks post-implantation in an animal that received a gene activated matrix containing pGAM1 plus pGAM2 plasmid DNA. Arrows point to radio-dense tissue in the gap (confirmed histologically to be bone).

5. DETAILED DESCRIPTION OF THE INVENTION

The present invention relates to an in vivo method for presentation and transfer of DNA into mammalian repair cells for the purpose of expressing therapeutic agents. The method of the invention involves implanting or placing gene activated matrices into a fresh wound site.

Wound healing is usually a coordinated, stereotyped sequence of events that includes (a) tissue disruption and loss of normal tissue architecture; (b) cell necrosis and hemorrhage; hemostasis (clot formation); (c) infiltration of segmented and mononuclear inflammatory cells, with vascular congestion and tissue edema; (d) dissolution of the clot as well as damaged cells and tissues by mononuclear cells (macrophages) (e) formation of granulation tissue (fibroplasia and angiogenesis). This sequence of cellular events has been observed in wounds from all tissues and organs generated in a large number of mammalian species (Gailet et al., 1994, Curr. Opin. Cell. Biol. 6:717–725). Therefore, the cellular sequence described above is a universal aspect of the repair of all mammalian tissues.

The invention is based on the discovery that repair cells involved in the wound healing process will naturally proliferate and migrate to the site of tissue injury and infiltrate the gene activated matrix. Surprisingly, these repair cells, which are normally difficult to efficiently transfect, either in vitro or in vivo, are extremely efficient at taking up and expressing DNA when activated to proliferate by the wound healing process.

Taking advantage of this feature, the methods of the present invention are designed to efficiently transfer, one or more DNA molecules encoding therapeutic agents to the proliferating repair cells. The methods involve the administration of a gene activated matrix containing DNA encoding translational products (i.e. therapeutic proteins) or transcriptional products (i.e. antisense or ribozymes) within a mammalian host at the site of a wound. The wound may arise from traumatic tissue injury, or alternatively, from tissue damage either induced by, or resulting from, surgical procedures.

As the proliferating repair cells migrate into and contact a gene activated matrix, they take up and express the DNA of interest thereby amplifying the amount of the therapeutic agent, protein or RNA. The transfected repair cells thereby serve as local bioreactors producing therapeutic agents that influence the local repair environment. For example, growth factors or cytokines produced by the transfected repair cells, will bind and stimulate targeted effector cells that express cognate cell surface receptors, thereby stimulating and amplifying the cascade of physiological events normally associated with the wound healing process.

Alternatively, the repair cells may take up and express DNA encoding proteins that inhibit the activity of antagonists of the wound healing process. The DNA may also encode antisense or ribozyme RNA molecules that may be used to inhibit translation of mRNAs encoding inflammatory proteins or other factors that inhibit wound healing or cause excessive fibrosis.

The gene activated matrix of the invention can be transferred to the patient using a variety of techniques. For example, when stimulating wound healing and regeneration, the matrices are transferred directly to the site of the wound, i.e., the fractured bone, injured connective tissue, etc. For use in skin repair, the matrices will be topically administered. For use in organ regeneration, the matrices will be surgically placed in a wound made in the organ.

Since the method of the invention is based on the natural migration and proliferation of repair cells into a wound site, and infiltration into the gene activated matrix located at the wound site, followed by the uptake of DNA, it is understood that the matrices must be transferred into a site in the body where the wound healing process has been induced.

One particularly important feature of the present invention is that the repair process may be engineered to result in either the formation of scar tissue and/or tissue regeneration. For example, the overexpression of the therapeutic proteins at the site of the wound, may result in regeneration of the injured tissue without the formation of scar tissue. In many instances, for example, such as bone repair, such regeneration is desirable because scar tissue is not optimally designed to support normal mechanical function. Alternatively, around a suture it may be desirable to form scar tissue to hold inherently weak tissue together. Therefore, the methods of invention may be used to stimulate wound healing either with, or without, the formation of scar tissue depending on the type and level of therapeutic protein expressed.

Direct plasmid DNA transfer from a matrix to a mammalian repair cell, through stimulation of the wound healing process, offers a number of advantages. First, the ease of producing and purifying DNA constructs compares favorably with traditional protein production method cost. Second, matrices can act as structural scaffolds that, in and of themselves, promote cell ingrowth and proliferation. Thus, they facilitate the targeting of repair cells for gene transfer. Third, direct gene transfer may be an advantageous method of drug delivery for molecules that normally undergo complex biosynthetic processing or for receptors which must be properly positioned in the cellular membrane. These types of molecules would fail to work if exogenously delivered to cells.

The present invention also relates to pharmaceutical compositions comprising matrices containing DNA for use in wound healing. The compositions of the invention are generally comprised of a biocompatible, or bone compatible, matrix material containing DNA encoding a therapeutic protein of interest.

The invention overcomes shortcomings specifically associated with current recombinant protein therapies for wound healing applications. First, direct gene transfer is a rational strategy that allows transfected cells to (a) make physiological amounts of therapeutic protein, modified in a tissue- and context-specific manner, and (b) deliver this protein to the appropriate cell surface signaling receptor under the appropriate circumstances. For reasons described above, exogenous delivery of such molecules is expected to be associated with significant dosing and delivery problems. Second, repeated administration, while possible, is not required with gene activated matrix technology: cell uptake of DNA can be controlled precisely with well-established sustained release delivery technologies, or, alternatively, integration of transfected DNA can be associated with long term recombinant protein expression.

The method of the invention can be universally applied to wounds that involve many different cells, tissues and organs; the repair cells of granulation tissue (Gailet et al., 1994, Curr. Opin. Cell. Biol. 6:717–725) are "targeted" where the method of the invention is used. The invention is demonstrated herein in three animal models (dog, rat and rabbit) and five tissues (bone, tendon, ligament, blood vessel and skeletal muscle), using three marker genes (β-galactosidase, luciferase and alkaline phosphatase), three promoter systems (CMV, RSV, LTR and SV40), two types of matrices (biological and synthetic). In all instances, repair cells that migrated into the gene activated matrix were successfully transfected. In particular, a functional outcome (bone growth) has been demonstrated following gene transfer to repair fibroblasts of a plasmid construct encoding either BMP-4, which acts as a signal transducing switch for osteoblast differentiation and growth (Wozney, 1992, Mol. Reprod. Dev. 32:160–167; Reddi, 1994, Curr. Opin. Genet. Deve. 4:737–744) or PTH1-34, which recruits osteoprogenitor cells (Orloff, et al, 1992, Endocrinology 131:1603–1611; Dempster et al., 1995 Endocrin Rev. 4:247–250).

5.1 THE GENE ACTIVATED MATRIX

Any biocompatible matrix material containing DNA encoding a therapeutic agent of interest, such as a translational product, i.e. therapeutic proteins, or transcriptional products, i.e. antisense or ribozymes, can be formulated and used in accordance with the invention.

The gene activated matrices of the invention may be derived from any biocompatible material. Such materials may include, but are not limited to, biodegradable or non-biodegradable materials formulated into scaffolds that support cell attachment and growth, powders or gels. Matrices may be derived from synthetic polymers or naturally occurring proteins such as collagen, other extracellular matrix proteins, or other structural macromolecules.

The DNA incorporated into the matrix may encode any of a variety of therapeutic proteins depending on the envisioned therapeutic use. Such proteins may include growth factors, cytokines, hormones or any other proteins capable of regulating the growth, differentiation or physiological function of cells. The DNA may also encode antisense or ribozyme molecules which inhibit the translation of proteins that inhibit wound repair and/or induce inflammation.

The transferred DNA need not be integrated into the genome of the target cell; indeed, the use of non-integrating DNA in the gene activated matrix is the preferred embodiment of the present invention. In this way, when the wound healing process is completed and the gene product is no longer needed, the gene product will not be expressed.

Therapeutic kits containing a biocompatible matrix and DNA form another aspect of the invention. In some instances the kits will contain preformed gene activated matrices thereby allowing the physician, to directly administer the matrix within the body. Alternatively, the kits may contain the components necessary for formation of a gene activated matrix. In such cases the physician may combine the components to form the gene activated matrices which may then be used therapeutically by placement within the body. In an embodiment of the invention the matrices may be used to coat surgical devices such as suture materials or implants. In yet another embodiment of the invention, gene activated matrices may include ready to use sponges, tubes, band-aids, lyophilized components, gels, patches or powders and telfa pads.

5.1.1 THE MATRIX MATERIALS

In one aspect of the invention, compositions are prepared in which the DNA encoding the therapeutic agent of interest is associated with or impregnated within a matrix to form a gene activated matrix. The matrix compositions function (i) to facilitate ingrowth of repair cells (targeting); and (ii) to harbor DNA (delivery). Once the gene activated matrix is prepared it is stored for future use or placed immediately at the site of the wound.

The type of matrix that may be used in the compositions, devices and methods of the invention is virtually limitless and may include both biological and synthetic matrices. The matrix will have all the features commonly associated with being "biocompatible", in that it is in a form that does not produce an adverse, allergic or other untoward reaction when administered to a mammalian host. Such matrices may be formed from both natural or synthetic materials. The matrices may be non-biodegradable in instances where it is desirable to leave permanent structures in the body; or biodegradable where the expression of the therapeutic protein is required only for a short duration of time. The matrices may take the form of sponges, implants, tubes, telfa pads, band-aids, bandages, pads, lyophilized components, gels, patches, powders or nanoparticles. In addition, matrices can be designed to allow for sustained release of the DNA over prolonged periods of time.

The choice of matrix material will differ according to the particular circumstances and the site of the wound that is to be treated. Matrices such as those described in U.S. Pat. No. 5,270,300, incorporated herein by reference, may be employed. Physical and chemical characteristics, such as, e.g., biocompatibility, biodegradability, strength, rigidity, interface properties and even cosmetic appearance may be considered in choosing a matrix, as is well known to those of skill in the art. Appropriate matrices will both deliver the DNA molecule and also act as an in situ scaffolding through which mammalian repair cells may migrate.

Where the matrices are to be maintained for extended periods of time, non-biodegradable matrices may be employed, such as sintered hydroxyapatite, bioglass, aluminates, other bioceramic materials and metal materials, particularly titanium. A suitable ceramic delivery system is that described in U.S. Pat. No. 4,596,574, incorporated herein by reference. The bioceramics may be altered in composition, such as in calcium-aluminate-phosphate; and they may be processed to modify particular physical and chemical characteristics, such as pore size, particle size, particle shape, and biodegradability. Polymeric matrices may also be employed, including acrylic ester polymers and lactic acid polymers, as disclosed in U.S. Pat. Nos. 4,521, 909, and 4,563,489, respectively, each incorporated herein by reference. Particular examples of useful polymers are those of orthoesters, anhydrides, propylene-cofumarates, or a polymer of one or more γ-hydroxy carboxylic acid monomers, e.g., γ-hydroxy auric acid (glycolic acid) and/or γ-hydroxy propionic acid (lactic acid).

A particularly important aspect of the present invention is its use in connection with orthopaedic implants and interfaces and artificial joints, including implants themselves and functional parts of an implant, such as, e.g., surgical screws, pins, and the like. In preferred embodiments, it is contemplated that the metal surface or surfaces of an implant or a portion thereof, such as a titanium surface, will be coated with a material that has an affinity for nucleic acids, most preferably, with hydroxyl apatite, and then the coated-metal will be further coated with the gene or nucleic acid that one wishes to transfer. The available chemical groups of the absorptive material, such as hydroxyl apatite, may be readily manipulated to control its affinity for nucleic acids, as is known to those of skill in the art.

In preferred embodiments, it is contemplated that a biodegradable matrix will likely be most useful. A biodegradable matrix is generally defined as one that is capable of being reabsorbed into the body. Potential biodegradable matrices for use in connection with the compositions, devices and methods of this invention include, for example, biodegradable and chemically defined calcium sulfate, tricalciumphosphate, hydroxyapatite, polyactic acid, polyanhidrides, matrices of purified proteins, and semipurified extracellular matrix compositions.

Other biocompatible biodegradable polymers that may be used are well known in the art and include, by way of example and not limitation, polyesters such as polyglycolides, polylactides and polylactic polyglycolic acid copolymers ("PLGA")(Langer and Folkman, 1976, Nature 263:797–800); polyethers such as polycaprolactone ("PCL"); polyanhydrides; polyalkyl cyanoacrylates such as n-butyl cyanoacrylate and isopropyl cyanoacrylate; polyacrylamides; poly(orthoesters); polyphosphazenes; polypeptides; polyurethanes; and mixtures of such polymers.

It is to be understood that virtually any polymer that is now known or that will be later developed suitable for the sustained or controlled release of nucleic acids may be employed in the present invention.

In preferred embodiments, the biocompatible biodegradable polymer is a copolymer of glycolic acid and lactic acid ("PLGA") having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

The length of the period of continuous sustained or controlled release of nucleic acids from the matrix according to the invention will depend in large part on the MW of the polymer and the composition ratio of lactic acid/glycolic acid. Generally, a higher ratio of lactic acid/glycolic acid, such as for example 75/25, will provide for a longer period of controlled of sustained release of the nucleic acids, whereas a lower ratio of lactic acid/glycolic acid will provide for more rapid release of the nucleic acids. Preferably, the lactic acid/glycolic acid ratio is 50/50.

The length of period of sustained or controlled release is also dependent on the MW of the polymer. Generally, a higher MW polymer will provide for a longer period of controlled or sustained release. In the case of preparing, for example, matrices providing controlled or sustained release for about three months, when the composition ratio of lactic acid/glycolic acid is 100/0, the preferable average MW of polymer ranges from about 7,000 to 25,000; when 90/10, from about 6,000 to 30,000; and when 80/20, from about 12,000 to 30,000.

Another type of biomaterial that may be used is small intestinal submucosa (SIS). The SIS graft material may be prepared from a segment of jejunum of adult pigs. Isolation of tissue samples may be carried out using routine tissue culture techniques such as those described in Badybak et al., 1989, J. Surg. Res. 47:74–80. SIS material is prepared by removal of mesenteric tissue, inversion of the segment, followed by removal of the mucosa and superficial submucosa by a mechanical abrasion technique. After returning the segment to its original orientation, the serosa and muscle layers are rinsed and stored for further use.

Another particular example of a suitable material is fibrous collagen, which may be lyophilized following extraction and partial purification from tissue and then sterilized. Matrices may also be prepared from tendon or dermal collagen, as may be obtained from a variety of commercial sources, such as, e.g., Sigma and Collagen Corporation. Collagen matrices may also be prepared as described in U.S. Pat. Nos. 4,394,370 and 4,975,527, each incorporated herein by reference.

In addition, lattices made of collagen and glycosaminoglycan (GAG) such as that described in Yannas & Burke, U.S. Pat. No. 4,505,266, may be used in the practice of the invention. The collagen/GAG matrix may effectively serve as a support or "scaffolding" structure into which repair cells may migrate. Collagen matrix, such as those disclosed in Bell, U.S. Pat. No. 4,485,097, may also be used as a matrix material.

The various collagenous materials may also be in the form of mineralized collagen. For example, the fibrous collagen implant material termed UltraFiber™, as may be obtained from Norian Corp., (1025 Terra Bella Ave., Mountain View, Calif., 94043) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils. Such a formulation may be employed in the context of delivering a nucleic acid segment to a bone tissue site. Mineralized collagen may be employed, for example, as part of gene activated matrix therapeutic kit for fracture repair.

At least 20 different forms of collagen have been identified and each of these collagens may be used in the practice of the invention. For example, collagen may be purified from hyaline cartilage, as isolated from diarthrodial joints or growth plates. Type II collagen purified from hyaline cartilage is commercially available and may be purchased from, e.g., Sigma Chemical Company, St. Louis. Type I collagen from rat tail tendon may be purchased from, e.g., Collagen Corporation. Any form of recombinant collagen may also be employed, as may be obtained from a collagen-expressing recombinant host cell, including bacterial yeast, mammalian, and insect cells. When using collagen as a matrix material it may be advantageous to remove what is referred to as the "telopeptide" which is located at the end of the collagen molecule and known to induce an inflammatory response.

The collagen used in the invention may, if desired be supplemented with additional minerals, such as calcium, e.g., in the form of calcium phosphate. Both native and recombinant type collagen may be supplemented by admixing, absorbing, or otherwise associating with, additional minerals in this manner.

5.1.2 THE DNA

The present methods and compositions may employ a variety of different types of DNA molecules. The DNA molecules may include genomic, cDNAs, single stranded DNA, double stranded DNA, triple stranded DNA, oligonucleotides and Z-DNA.

The DNA molecules may code for a variety of factors that promote wound healing including extracellular, cell surface, and intracellular RNAs and proteins. Examples of extracellular proteins include growth factors, cytokines therapeutic proteins, hormones and peptide fragments of hormones, inhibitors of cytokines, peptide growth and differentiation factors, interleukins, chemokines, interferons, colony stimulating factors and angiogenic factors. Examples of such proteins include, but are not limited to, the superfamily of TGF-$\beta$ molecules, including the five TGF-$\beta$ isoforms and bone morphogenetic proteins (BMP), latent TGF-$\beta$ binding proteins, LTBP; keratinocyte growth factor (KGF); hepatocyte growth factor (HGF); platelet derived growth factor (PDGF); insulin-like growth factor (IGF); the basic fibroblast growth factors (FGF-1, FGF-2 etc.), vascular endothelial growth factor (VEGF); Factor VIII and Factor IX; erythropoietin (EPO); tissue plasminogen activator (TPA); activins and inhibins. Hormones which may be used in the practice of the invention include growth hormone (GH) and parathyroid hormone (PTH). Examples of extracellular proteins also include the extracellular matrix proteins such as collagen, laminin, and fibronectin. Examples of cell surface proteins include the family of cell adhesion molecules (e.g., the integrins, selectin, Ig family members such as N-CAM and L1, and cadherins); cytokine signaling receptors such as the type I and type II TGF-$\beta$ receptors and the FGF receptor; and non-signaling co-receptors such as betaglycan and syndecan. Examples of intracellular RNAs and proteins include the family of signal transducing kinases, cytoskeletal proteins such as talin and vinculin, cytokine binding proteins such as the family of latent TGF-$\beta$ binding proteins, and nuclear trans acting proteins such as transcription factors and enhancing factors.

The DNA molecules may also code for proteins that block pathological processes, thereby allowing the natural wound healing process to occur unimpeded. Examples of blocking factors include ribozymes that destroy RNA function and DNAs that, for example, code for tissue inhibitors of enzymes that destroy tissue integrity, e.g., inhibitors of metalloproteinases associated with arthritis.

One may obtain the DNA segment encoding the protein of interest using a variety of molecular biological techniques, generally known to those skilled in the art. For example, cDNA or genomic libraries may be screened using primers or probes with sequences based on the known nucleotide sequences. Polymerase chain reaction (PCR) may also be used to generate the DNA fragment encoding the protein of interest. Alternatively, the DNA fragment may be obtained from a commercial source.

Genes with sequences that vary from those described in the literature are also encompassed by the invention, so long as the altered or modified gene still encodes a protein that functions to stimulate wound healing in any direct or indirect manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art. Such modifications include the deletion, insertion or substitution of bases which result in changes in the amino acid sequence. Changes may be made to increase the activity of an encoded protein, to increase its biological stability or half-life, to change its glycosylation pattern, confer temperature sensitivity or to alter the expression pattern of the protein and the like. All such modifications to the nucleotide sequences are encompassed by this invention.

The DNA encoding the translational or transcriptional products of interest may be recombinantly engineered into variety of vector systems that provide for replication of the DNA in large scale for the preparation of gene activated matrices. These vectors can be designed to contain the necessary elements for directing the transcription and/or translation of the DNA sequence taken up by the repair cells at the wound in vivo.

Vectors that may be used include, but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18–23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Vectors that allow for the in vitro transcription of RNA, such as SP6 vectors, may also be used to produce large quantities of RNA that may be incorporated into matrices. Alternatively, recombinant virus vectors including, but not limited to those derived from viruses such as herpes virus, retroviruses, vaccinia viruses, adenoviruses, adeno-associated viruses or bovine papilloma virus may be engineered. While integrating vectors may be used, non-integrating systems, which do not transmit the gene product to daughter cells for many generations are preferred for wound healing. In this way, the gene product is expressed during the wound healing process, and as the gene is diluted out in progeny generations, the amount of expressed gene product is diminished.

Methods which are well known to those skilled in the art can be used to construct expression vectors containing the protein coding sequence operatively associated with appropriate transcriptional/translational control signals. These methods include in vitro recombinant DNA techniques, and synthetic techniques. See, for example, the techniques described in Sambrook, et al., 1992, Molecular Cloning, A Laboratory Manual, Cold Spring Harbor Laboratory, N.Y. and Ausubel et al., 1989, Current Protocols in Molecular Biology, Greene Publishing Associates & Wiley Interscience, N.Y.

The genes encoding the proteins of interest may be operatively associated with a variety of different promoter/enhancer elements. The expression elements of these vectors may vary in their strength and specificities. Depending on the host/vector system utilized, any one of a number of suitable transcription and translation elements may be used. The promoter may be in the form of the promoter which is naturally associated with the gene of interest. Alternatively, the DNA may be positioned under the control of a recombinant or heterologous promoter, i.e., a promoter that is not normally associated with that gene. For example, tissue specific promoter/enhancer elements may be used to regulate the expression of the transferred DNA in specific cell types. Examples of transcriptional control regions that exhibit tissue specificity which have been described and could be used, include but are not limited to: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:42S–51S); insulin gene control region which is active in pancreatic beta cells (Hanahan, 1985, Nature 315:115–122); immunoglobulin gene control region which is active in lymphoid cells (Grosschedl et al., 1984, Cell 38:647–658; Adams et al., 1985, Nature 318:533–538; Alexander et al., 1987, Mol. Cell. Biol. 7:1436–1444): albumin gene control region which is active in liver (Pinkert et al., 1987, Genes and Devel. 1:268–276) alpha-fetoprotein gene control region which is active in liver (Krumlauf et al., 1985, Mol. Cell. Biol. 5:1639–1648; Hammer et al., 1987, Science 235:53–58); alpha-1-antitrypsin gene control region which is active in liver (Kelsey et al., 1987, Genes and Devel. 1:161–171); beta-globin gene control region which is active in myeloid cells (Magram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286); and gonadotropic releasing hormone gene control region which is active in the hypothalamus (Mason et al., 1986, Science 234:1372–1378). Promoters isolated from the genome of viruses that grow in mammalian cells, (e.g., RSV, vaccinia virus 7.5K, SV40, HSV, adenoviruses MLP, MMTV LTR and CMV promoters) may be used, as well as promoters produced by recombinant DNA or synthetic techniques.

In some instances, the promoter elements may be constitutive or inducible promoters and can be used under the appropriate conditions to direct high level or regulated expression of the gene of interest. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, etc.

In addition to DNA sequences encoding therapeutic proteins of interest, the scope of the present invention includes the use of ribozymes or antisense DNA molecules that may be transferred into the mammalian repair cells. Such ribozymes and antisense molecules may be used to inhibit the translation of RNA encoding proteins of genes that inhibit a disease process or the wound healing process thereby allowing tissue repair to take place.

The expression of antisense RNA molecules will act to directly block the translation of mRNA by binding to targeted mRNA and preventing protein translation. The expression of ribozymes, which are enzymatic RNA molecules capable of catalyzing the specific cleavage of RNA may also be used to block protein translation. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RNA sequences. RNA molecules may be generated by transcription of DNA sequences encoding the RNA molecule.

It is also within the scope of the invention that multiple genes, combined on a single genetic construct under control of one or more promoters, or prepared as separate constructs of the same or different types may be used. Thus, an almost endless combination of different genes and genetic constructs may be employed. Certain gene combinations may be designed to, or their use may otherwise result in, achieving synergistic effects on cell stimulation and regeneration, any and all such combinations are intended to fall within the scope of the present invention. Indeed, many synergistic effects have been described in the scientific literature, so that one of ordinary sill in the art would readily be able to identify likely synergistic gene combinations, or even gene-protein combinations.

5.1.3 PREPARATION OF THE GENE ACTIVATED MATRICES

In preferred embodiments, matrix or implant material is contacted with the DNA encoding a therapeutic product of interest by soaking the matrix material in a recombinant DNA stock solution. The amount of DNA, and the amount of contact time required for incorporation of the DNA into the matrix, will depend on the type of matrix used and can be readily determined by one of ordinary skill in the art without undue experimentation. Alternatively, the DNA may be encapsulated within a matrix of synthetic polymers, such as, for example, block copolymers of polyactic-polyglycolic acid (See Langer and Folkman, 1976 Nature, 263:797–800 which is incorporated herein by reference). Again, these parameters can be readily determined by one of ordinary skill in the art without undue experimentation. For example, the amount of DNA construct that is applied to the matrix will be determined considering various biological and medical factors. One would take into consideration the particular gene, the matrix, the site of the wound, the mammalian host's age, sex and diet and any further clinical factors that may effect wound healing such as the serum levels of various factors and hormones.

In additional embodiments of the invention compositions of both biological and synthetic matrices and DNA may be lyophilized together to form a dry pharmaceutical powder. The gene activated matrix may be rehydrated prior to implantation in the body, or alternatively, the gene activated matrix may become naturally rehydrated when placed in the body.

In some instances medical devices such as implants, sutures, wound dressings, etc. may be coated with the nucleic acid compositions of the invention using conventional coating techniques as are well known in the art. Such methods include, by way of example and not limitation, dipping the device in the nucleic acid composition, brushing the device with the nucleic acid composition and/or spraying the device with the aerosol nucleic acid compositions of the invention. The devide is then dried, either at room temperature or with the aid of a drying oven, optionally at reduced pressure. A preferred method for coating sutures is provided in the examples.

For sutures coated with a polymeric matrix containing plasmid DNA, applicants have discovered that applying a coating composition containing a total of about 0.01 to 10 mg plasmid DNA and preferably about 1 to 5 mg plasmid DNA, to a 70 cm length of suture using about 5 to 100, preferably about 5 to 50, and more preferably about 15 to 30 coating applications yields a therapeutically effective and uniform coating.

In a particularly preferred embodiment, the invention provides coated sutures, especially sutures coated with a polymeric matrix containing nucleic acids encoding therapeutic proteins that stimulate wound healing in vivo.

Sutures which may be coated in accordance with the methods and compositions of the present invention include any suture of natural or synthetic origin. Typical suture materials include, by way of example and not limitation, silk; cotton; linen; polyolefins such as polyethylene and polypropylene; polyesters such as polyethylene terephthalate; homopolymers and copolymers of hydroxycarboxylic acid esters; collagen (plain or chromicized); catgut (plain or chromicized); and suture-substitutes such as cyanoacrylates. The sutures may take any convenient form such as braids or twists, and may have a wide range of sizes as are commonly employed in the art.

The advantages of coated sutures, especially sutures coated with a polymeric matrix containing nucleic acids encoding therapeutic proteins that stimulate wound healing cover virtually every field of surgical use in humans and animals.

5.2. USES OF THE GENE ACTIVATED MATRIX

The invention is applicable to a wide variety of wound healing situations in human medicine. These include, but are not limited to, bone repair, tendon repair, ligament, repair, blood vessel repair, skeletal muscle repair, and skin repair. For example, using the gene activated matrix technology, cytokine growth factors produced by transfected repair cells will influence other cells in the wound, through binding of cell surface signaling receptors, thereby stimulating and amplifying the cascade of physiological events normally associated with the process of wound healing. The end result is the augmentation of tissue repair and regeneration.

The method of the invention also is useful when the clinical goal is to block a disease process, thereby allowing natural tissue healing to take place, or when the goal is to replace a genetically defective protein function.

Wounds may arise from traumatic injury, or alternatively, from tissue damage either induced by, or resulting from, a surgical procedure. The gene activated matrix of the invention can be transferred to the patient using various techniques. For example, matrices can be transferred directly to the site of the wound by the hand of the physician, either as a therapeutic implant or as a coated device (e.g., suture, stent, coated implant, etc.). Matrices can be topically administered, either as placed surgically in a normal tissue site in order to treat diseased tissue some distance away.

The process of wound healing is a coordinated sequence of events which includes, hemorrhage, clot formation, dissolution of the clot with concurrent removal of damaged tissue, and deposition of granulation tissue as initial repair material. The granulation tissue is a mixture of fibroblasts and capillary blood vessels. The wound healing process involves diverse cell populations including endothelial cells, stem cells, macrophages and fibroblasts. The regulatory factors involved in wound repair are known to include systemic hormones, cytokines, growth factors, extracellular matrix proteins and other proteins that regulate growth and differentiation.

The DNA transfer methods and matrix compositions of the present invention will have a wide range of applications as a drug delivery method for stimulating tissue repair and regeneration in a variety of different types of tissues. These include but are not limited to bone repair, skin repair, connective tissue repair, organ regeneration, or regulation of vasculogenesis and/or angiogenesis. The use of gene activated matrices may also be used to treat patients with impaired healing capacity resulting from, for example, the effects of aging or diabetes. The matrices may also be used for treatment of wounds that heal slowly due to natural reasons, e.g., in the elderly, and those who do not respond to existing therapies, such as in those individuals with chronic skin wounds.

One important feature of the present invention is that the formation of scar tissue at the site of the wound may be regulated by the selective use of gene activated matrices. The formation of scar tissue may be regulated by controlling the levels of therapeutic protein expressed. In instances, such as the treatment of burns or connective tissue damage it is especially desirable to inhibit the formation of scar tissue.

The methods of the present invention include the grafting or transplantation of the matrices containing the DNA of interest into the host. Procedures for transplanting the matrices may include surgical placement, or injection, of the matrices into the host. In instances where the matrices are to be injected, the matrices are drawn up into a syringe and injected into a patient at the site of the wound. Multiple injections may be made in the area of the wound. Alternatively, the matrices may be surgically placed at the site of the wound. The amount of matrices needed to achieve the purpose of the present invention i.e. stimulation of wound repair and regeneration, is variable depending on the size, age and weight of the host.

It is an essential feature of the invention that whenever a gene activated matrix is transferred to the host, whether by injection or surgery, that the local tissue damage be sufficient enough to induce the wound healing process. This is a necessary prerequisite for induction of migration and proliferation of the targeted mammalian repair cells to the site of the gene activated matrix.

Specific embodiments are described in the sections that follow.

5.3. BONE REGENERATION

Bone has a substantial capacity to regenerate following fracture. The complex but ordered fracture repair sequence includes hemostasis, clot dissolution, granulation tissue ingrowth, formation of a callus, and remodeling of the callus to an optimized structure (A. W. Ham., 1930, J. Bone Joint Surg. 12, 827–844). Cells participating in this process include platelets, inflammatory cells, fibroblasts, endothelial cells, pericytes, osteoclasts, and osteogenic progenitors. Recently, several peptide growth and differentiation factors have been identified that appear to control cellular events associated with bone formation and repair (Erlebacher, A., et al., 1995, Cell 80, 371–378). Bone morphogenetic proteins (BMPs), for example, are soluble extracellular factors that control osteogenic cell fate: BMP genes are normally expressed by cultured fetal osteoblasts (Harris, S. E., et al., 1994, J. Bone Min. Res. 9, 389–394) and by osteoblasts during mouse embryo skeletogenesis (Lyons, K. M., et al., 1989, Genes Dev. 3, 1657–1668; Lyons, K. M., et al., 1990, Development 190, 833–844; Jones, M. C., et al., 1991, Development 111, 531–542), recombinant BMP proteins initiate cartilage and bone progenitor cell differentiation (Yamaguchi, A., et al., 1991, J. Cell Biol. 113, 681–687; Ahrens, M., et al., 1993, J. Bone Min. Res. 12, 871–880; Gitelman, S. E., et al., 1994, J. Cell Biol. 126, 1595–1609; Rosen, V., et al., 1994, J. Cell Biol. 127, 1755–1766), delivery of recombinant BMPs induce a bone formation sequence similar to endochondral bone formation (Wozney, J. M., 1992, Mol. Reprod. Dev. 32, 160–167; Reddi, A. H., 1994, Curr. Opin. Genet. Dev. 4, 737–744), and BMP-4 gene expression is unregulated early in the process of fracture repair (Nakase, T., et al., 1994, J. Bone Min. Res. 9, 651–659). Osteogenic protein-1, a member of a family of molecules related to the BMPs (Ozkaynak, E., et al., 1990, EMBO J. 9, 2085–2093), is capable of similar effects in vitro and in vivo (Sampath, T. K., et al., 1992, J. Biol. Chem. 267, 20352–20362; Cook, S. D., et al., (1994) J. Bone Joint Surg. 76-A, 827–838). TGF-$\beta$ has also been shown to stimulate cartilage and bone formation in vivo (Centrella, M., et al., 1994, Endocrine Rev. 15, 27–38; Sumner, D. R., et al., 1995, J. Bone Joint Surg. 77A, 1135–1147). Finally, parathyroid hormone (PTH) is an 84 amino acid hormone that raises the plasma and extracellular fluid $Ca^{+2}$ concentration. In skeletal tissues, intermittent administration of a PTH fragment-possessing the structural requirements for biological activity (aa 1–34) produces a true anabolic effect: numerous in vivo and in vitro studies provide strong evidence that PTH1-34 administration in animals (including rats) results in uncoupled, high-quality bone formation due to a combined inhibitory effect on osteoclasts and stimulatory effect on osteogenic cells (Dempster, D. W., et al., 1993, Endocrine Rev. 14, 690–709). The PTH1-34 peptide is known to interact synergistically with BMP-4, which up-regulates the expression of functional cell surface PTH receptors in differentiating osteoblasts in vitro (Ahrens, M., et al., 1993, J. Bone Min. Res. 12, 871–880).

As recombinant proteins, peptide growth and differentiation factors such as BMP and TGF-$\beta$1 represent promising therapeutic alternatives for fracture repair (Wozney, J. M., 1992, Mol. Reprod. Dev. 32, 160–167; Reddi, A. H., 1994, Curr. Opin. Genet. Dev. 4, 737–744; Centrella, M., et al., 1994, Endocrine Rev. 15, 27–38; Sumner, D. R., et al., 1995 J. Bone Joint Surg. 77-A, 1135–1147). However, relatively large doses (microgram amounts) are required to stimulate significant new bone formation in animals, raising the concern that future human therapies may be expensive and may possess an increased risk of toxicity.

In an embodiment of the invention, gene activated matrices are surgically implanted into a 5 mm osteomy site in the rat, a model of a complex, non-healing fracture in humans. The present inventors have found that gene transfer to repair cells in the osteotomy gap could be readily achieved.

Defects in the process of bone repair and regeneration are associated with significant complications in clinical orthopaedic practice, for example, fibrous non-union following bone fracture, implant interface failures and large allograft failures. Many complex fractures are currently treated using autografts but this technique is not effective and is associated with complications.

Naturally, any new technique designed to stimulate bone repair would be a valuable tool in treating bone fractures. A significant portion of fractured bones are still treated by casting, allowing natural mechanisms to effect wound repair. Although there have been advances in fracture treatment in recent years, including improved devices, the development of new processes to stimulate, or complement, the wound repair mechanisms would represent significant progress in this area.

The present invention may be used to transfer a bone growth gene to promote fracture repair. Other important aspects of this technology include the use of gene transfer to treat patents with "weak bones", such as in diseases like osteoporosis; to improve poor healing which may arise for unknown reasons, e.g., fibrous non-union; to promote implant integration and the function of artificial joints; to stimulate healing of other skeletal tissues such as Achilles tendon; and as an adjuvant to repair large defects.

Bone tissue is known to have the capacity for repair and regeneration and there is a certain understanding of the cellular and molecular basis of these processes. The initiation of new bone formation involves the commitment, clonal expansion, and differentiation of repair cells. Once initiated, bone formation is promoted by a variety of polypeptide growth factors. Newly formed bone is then maintained by a series of local and systemic growth and differentiation factors.

Several bone morphogenetic protein genes have now been cloned (Wozney et al., 1988; Rosen et al. 1989, Connect. Tissue Res., 20:313:319; summarized in Alper, 1994) and this work has established BMPs as members of the transforming growth factor-β (TGF-β) superfamily based on DNA sequence homologies. The cloning of distinct BMP genes has led to the designation of individual BMP genes and proteins as BMP-1 through at least BMP-8. BMPs 2–8 are generally thought to be osteogenic while BMP-1 may be a more generalized morphogen; Shimell et al., 1991, Cell, 67:469–481). BMP-3 is also called osteogen (Luyten et al., 1989, J. Biol. Chem., 264:13377–13380) and BMP-7 is also called OP-1 (Ozkaynak et al., 1990, EMBO J., 9:2085–2093). TGFs and BMPs each act on cells via complex, tissue-specific interactions with families of cell surface receptors (Roberts & Sporn, 1989, M. B. Sporn and A. B. Roberts, Eds., Springer-Verlag, Heidelberg, 95 (Part 1); Aralkar et al., 1991).

Transforming growth factors (TGFs) have also been shown to have a central role in regulating tissue healing by affecting cell proliferation, gene expression, and matrix protein synthesis (Roberts & Sporn, 1989, M. B. Sporn and A. B. Roberts, Eds., Springer-Verlag, Heidelberg, 95 (Part 1)). For example, TGF-β1 and TGF-β2 can initiate both chondrogenesis and osteogenesis (Joyce et al., 1990, J. Cell Biol., 110:195–2007; Izumi et al., 1992, J. Bone Min. Res., 7:115–11; Jingushi et al., 1992, J. Orthop. Res., 8:364–371).

Other growth factors/hormones besides TGF and BMP can be used in the practice of the invention to influence new bone formation following fracture. For example, fibroblast growth factor injected into a rat fracture site (Jingushi et al., 1990) at multiple high doses (1.0. mg/50 ml) resulted in a significant increase in cartilage tissue in the fracture gap, while lower doses had no effect.

Calcium regulating hormones such as parathyroid hormone (PTH) may also be used in one aspect of the invention.

PTH is an 84 amino acid calcium-regulated hormone whose principal function is to raise $Ca^{+2}$ concentration in plasma and extracellular fluid. Intact PTH was also shown to stimulate bone reabsorption in organ culture over 30 years ago, and the hormone is known to increase the number and activity of osteoclasts. Studies with the native hormone and with synthetic peptides have demonstrated that the amino terminus of the molecule (aa-1–34) contains the structural requirements for biological activity (Tregear et al., 1973; Hermann-Erlee et al., 1976, Endocrine Research Communications, 3:21–35; Riond, 1993, Clin. Sci., 85:223–228).

In an embodiment of the invention the gene activated matrices are surgically implanted into the site of the bone fracture. Such surgical procedures may include direct injection of a GAM preparation into the fracture site, the surgical repair of a complex fracture, or arthroscopic surgery. In instances where the gene activated matrices are being used to repair fractured bone, the mammalian repair cells will naturally migrate and proliferate at the site of bone damage.

The present inventors have surprisingly found that gene transfer into repair cells in the regenerating tissue in the osteotomy gap could be readily achieved. Currently, the preferred methods for achieving gene transfer generally involve using a fibrous collagen implant material soaked in a solution of DNA shortly before being placed in the site in which one desires to promote bone growth or using a preparation of plasmid DNA encapsulated in a synthetic matrix such as a block copolymer of PLGA. As the studies presented herein show, the implant material facilitates the targeted uptake of exogenous plasmid constructs by cells in the osteotomy gap, which clearly participate in bone regeneration/repair. The transgenes, following cellular uptake, direct the expression of recombinant polypeptides, as evidenced by the in vivo expression of functional marker gene products.

Further studies are presented herein demonstrating that the transfer of an osteotropic gene results in cellular expression of a recombinant osteotropic molecule, which expression is directly associated with stimulation of new bone formation. Specifically, a gene transfer vector coding for BMP-4 and a gene transfer vector encoding a fragment of human PTH1-34, alone and in combination, will stimulate new bone formation. After considering a relatively large number of candidate genes, a gene transfer vector coding for a fragment of human parathyroid hormone, hPTH1-34, will stimulate new bone formulation in Sprague-Dawley rats, indicating that the human peptide can efficiently bind the PTH/PTHrP receptor on the rat osteoblast cell surface.

5.4. SOFT TISSUES

The present invention may also be used to stimulate the growth or regeneration of soft tissues such as ligament, tendon, cartilage and skin. Skeletal connective tissue damage due to traumatic injury may be treated using matrices containing genes encoding a variety of growth factors. Connective tissue normally consists of cells and extracellular matrix organized in a characteristic tissue architecture. Tissue wounding can disrupt this architecture and stimulate a wound healing response. The methods of the present invention are particularly well suited for stimulation of growth and regeneration of connective tissue as it is important that the injured tissue regenerate without the formation of scar tissue as scar tissue can interfere the normal mechanical function of connective tissue.

Various growth factors may be used to promote soft tissue repair. These include, but are not limited to, members of the TGF-β superfamily (e.g., TGF-β itself), which stimulates expression of genes coding for extracellular matrix proteins, and other cytokines such as EGF and PDGF. Examples of other genes that may be used include (a) cytokines such as the peptide growth and differentiation factors, interleukines, chemokines, interferons, colony stimulating factors; (b) angiogenic factors such as FGF and VEGF; (c) extracellular matrix proteins such as collagen, laminin, and fibronectin; (d) the family of cell adhesion molecules (e.g., the integrins, selectins, Ig family members such as N-CAM and L1, and cadherins); (e) cell surface cytokine signaling receptors such as the type I and type II TGF-β receptors and the FGF receptors; (f) non-signaling co-receptors such as betaglycan and syndecan; (g) the family of signal transducing kinases; (h) cytoskeletal proteins such as talin and vinculin; (i) cytokine binding proteins such as the family of latent TGF-β binding proteins; and (j) nuclear trans acting proteins such as transcription factors.

Once formed, such matrices, may then be placed in the host mammal in the area of the connective tissue wound. The gene activated matrices may be injected directly into the area of connective tissue injury. Alternatively, surgical techniques, such as arthroscopic surgery, may be used to deliver the matrices to the area of the connective tissue wound.

5.5. ORGAN REGENERATION

The present invention may also be used to stimulate the repair and regeneration of organ tissue. Organ damage due to traumatic injury, or surgery, may be treated using the methods of the present invention. In the case of liver, the liver may be damaged due to excessive alcohol consumption or due to infection with various types of infectious agents such as the hepatitis family of viruses. The kidney may likewise fail to function normally as a result of damage resulting from kidney disease. Mucous membranes of the esophagus, stomach or duodenum may contain ulcerations caused by acid and pepsin in gastric juices. The ulcerations may also arise from colonization of gastric mucosal cells with *Helicobacter pylori* bacteria. These organs and diseases serve only as examples, indeed the methods of the invention may be used to treat diseases, or to stimulate organ regeneration in any organ of the body.

Matrices containing DNA encoding cytokines which stimulate proliferation and differentiation of cells, and/or regulate tissue morphogenesis, may be transplanted to the appropriate organ site. Such factors may include but are not limited to, the transforming growth factor family of proteins, platelet derived growth factor (PDGF), insulin like growth factor (IGF) and fibroblast growth factory (FGF). In some instances it may be useful to express growth factors and/or cytokines that stimulate the proliferation of cell types specific for a given organ, i.e., hepatocytes, kidney or cardiac cells, etc. For example, hepatocyte growth factor may be expressed to stimulate the wound healing process in the liver. For treatment of ulcers, resulting from Helicobacter infection, the gene activated matrices may contain DNA encoding anti-microbial proteins.

The gene activated matrices of the invention can be surgically implanted into the organ that is to be treated. Alternatively, laproscopic surgical procedures may be utilized to transfer the gene activated matrices into the body. In cases where the treatment is in response to tissue injury, the natural wound healing process will stimulate the migration and proliferation of the repair cells to the transplanted matrices. Alternatively, where the gene activated matrices are transferred to organs which have not been injured, for example, where matrices are implanted to express therapeutic proteins not involved in wound healing, the wound healing process can be stimulated by induction of tissue injury.

5.6. REGULATION OF ANGIOGENESIS

The present invention may also be used to regulate the formation and spreading of blood vessels, or vasculogenesis and angiogenesis, respectively. Both these physiological processes play an important role in wound healing and organ regeneration.

Initially, at the site of a wound, granulation tissue which is a mixture of collagen, matrix and blood vessels, is deposited and provides wound strength during tissue repair. The formation of new blood vessels involves the proliferation, migration and infiltration of vascular endothelial cells, and is known to be regulated by a variety of polypeptide growth factors. Several polypeptides with endothelial cell growth promoting activity have been identified, including acidic and basic fibroblastic growth factors (FGF), vascular endothelial growth factor (VEGF), and placental derived growth factor (PDGF).

To stimulate the formation and spreading of blood vessels, DNA encoding such growth factors may be incorporated into matrices and these matrices may be implanted into the host. In some instances, it may be necessary to induce the wound healing process through tissue injury.

It may be desirable to inhibit the proliferation of blood vessel formation, such as in angiogenesis associated with the growth of solid tumors which rely on vascularization for growth. Tumor angiogenesis may be inhibited through the transfer of DNA's encoding negative inhibitors of angiogenesis, such as thrombospondin or angiostatin. In specific embodiments of the invention, DNA encoding, for example, thrombospondin or angiostatin, may be incorporated into a matrix followed by the implanting of the matrix into a patient at the site of the tumor.

5.7. REPAIR OF THE SKIN

The present invention may also be used to stimulate the growth and repair of skin tissue. In wounds which involve injury to areas of the skin, and particularly in the case of massive burns, it is important that the skin grow very rapidly in order to prevent infections, reduce fluid loss, and reduce the area of potential scarring. Skin damage resulting from burns, punctures, cuts and/or abrasions may be treated using the gene activated matrices of the present invention. Skin disorders such as psoriasis, atopic dermatitis or skin damage arising from fungal, bacterial and viral infections or treatment of skin cancers such as melanoma, may also be treated using the methods of the invention.

Matrices containing DNA encoding cytokines which stimulate proliferation and differentiation of cells of the skin, including central basal stem cells, keratinocytes, melanoytes, Langerhans cells and Merkel cells may be used to treat skin injuries and disorders. The gene activated matrices serve two functions, the protection of the wound from infection and dehydration and supplying the DNA for uptake by repair cells. The gene activated matrices of the invention may include dermal patches, cadaver skin, band-aids, gauze pads, collagen lattices such as those disclosed in U.S. Pat. No. 4,505,266 or U.S. Pat. No. 4,485,097, topical creams or gels. Prior to the application of the matrices to the wound site, damaged skin or devitalized tissue may be removed. The DNA to be incorporated into the matrices may encode a variety of different growth factors including keratinocyte-growth-factor (KGF) or epidermal growth factor (EGF). DNA encoding IL-1 which has been shown to be a potent inducer of epithelial cell migration and proliferation as part of the healing process may also be incorporated into the matrices of the invention.

6. EXAMPLE: IMPLANT MATERIAL FOR USE IN BONE GENE TRANSFER

Various implant materials may be used for transferring genes into the site of bone repair and/or regeneration in vivo. These materials are soaked in a solution containing the DNA or gene that is to be transferred to the bone regrowth site. Alternatively, DNA may be incorporated into the matrix as a preferred method of making.

One particular example of a suitable material is fibrous collagen, which may be lyophilized following extraction and partial purification from tissue and then sterilized. Another particularly preferred collagen is type II collagen, with the most particularly preferred collagen being either recombinant type II collagen, or mineralized type II collagen. Prior to placement in osteotomy sites, implant materials are soaked in solutions of DNA (or virus) under sterile conditions. The soaking may be for any appropriate and convenient period, e.g., from 6 minutes to over-night. The DNA (e.g., plasmid) solution will be a sterile aqueous solution, such as sterile water or an acceptable buffer, with the concentration generally being about 0.5–1.0 mg/ml. Currently preferred plasmids are those such as pGL2 (Promega), pSV40β-gal, pAd.CMVlacZ, and pcDNA3.

7. EXAMPLE: IN VIVO PROTEIN DETECTION FOLLOWING TRANSGENE EXPRESSION

7.1. β-GALACTOSIDASE TRANSGENE

Bacterial β-galactosidase can be detected immunohistochemically. Osteotomy tissue specimens were fixed in Bouins fixative, demineralized, and then split in half along the longitudinal plane. One-half of each specimen was embedded in paraffin for subsequent immunohistochemical identification of the bacterial β-galactosidase protein.

For immunohistochemistry, cross-Sections (2–3 mm thick) were transferred to poly-L-Lysine coated microscope slides and fixed in acetone at 0° C. for at least 20 min. Sections were rehydrated in PBS. Endogenous peroxidase activity was quenched by immersion of tissue sections in 0.1% hydrogen peroxide (in 95% methanol) at room temperature for 10 min, and quenched sections were washed 3x in PBS. In some cases, sectioned calvariae were demineralized by immersion in 4% EDTA, 5% polyvinyl pyrrolidone, and 7% sucrose, pH 7.4, for 24 h at 4° C. Demineralized sections were washed 3x before application for antibodies. Primary antibodies were used without dilution in the form of hybridoma supernatant. Purified antibodies were applied to tissue sections at a concentration of 5 mg/ml. Primary antibodies were detected with biotinylated rabbit antimouse IgG and peroxidase conjugated streptavidin (Zymed Histostain-SPkit). After peroxidase staining, sections were counterstained with hematoxylin.

Bacterial β-gal was also detected by substrate utilization assays using commercially available kits (e.g., Promega) according to the manufacturers' instructions.

7.2. LUCIFERASE TRANSGENE

Luciferase was detected by substrate utilization assays using commercially available kits (e.g., Promega) according to the manufacturers' instructions.

7.3. PTH TRANSGENES

Recombinant PTH, such as hPTH1-34 peptide, was assayed in homogenates of osteotomy gap tissue, for example, using two commercially available radioimmunoassay kits according to the manufacturer's protocols (Nichols Institute Diagnostics, San Juan Capistrano, Calif.).

One kit is the Intact PTH-Parathyroid Hormone 100T Kit. This radioimmunoassay utilizes an antibody to the carboxy terminus of the intact hormone, and this is used to measure endogenous levels of hormone in gap osteotomy tissue. This assay may be used to establish a baseline value PTH expression in the rat osteotomy model.

The second kit is a two=site immunoradiometric kit for the measurement of rat PTH. This kit uses affinity purified antibodies specific for the amino terminus of the intact rat hormone (PTH1-34) and thus will measure endogenous PTH production as well as the recombinant protein. Previous studies have shown that these antibodies cross-react with human PTH and this are able to recognize recombinant molecules in vivo.

Values obtained with kit #1 (antibody to the carboxy terminus) were subtracted from values obtained with kit #2 (antibody to the amino terminus) to obtain an accurate and sensitive measurements. The level of recombinant peptide was thus correlated with the degree of new bone formation.

7.4. BMP TRANSGENE

BMP proteins, such as the murine BMP-4 transgene peptide product, were detected immunohistochemically using a specific antibody that recognizes the HA epitope (Majmudar et al., 1991, J. Bone and Min. Res. 6:869–881), such as the monoclonal antibody available from Boehringer-Mannheim. Antibodies to BMP proteins themselves may also be used. Such antibodies, along with various immunoassay methods, are described in U.S. Pat. No. 4,857,456, incorporated herein by reference.

Osteotomy tissue specimens were fixed in Bouins fixative, demineralized, and then split in half along the longitudinal plane. One-half of each specimen was embedded in paraffin for subsequent immunohistochemical identification of the recombinant murine BMP-4 molecule.

8. EXAMPLE: TRANSFER OF AN OSTEOTROPIC GENE STIMULATES BONE REGENERATION/REPAIR IN VIVO

The following experiment was designed to investigate whether gene transfer could be employed to create transfected cells that constitutively express recombinant hPTH1-34 in vivo, and whether this transgene can stimulate bone formation. The rate of new bone formation was analyzed as follows. At necropsy the osteotomy site was carefully dissected for histomorphometric analysis. The A-P and M-L dimensions of the callus tissue are measured using calipers. Specimens were then immersion fixed in Bouins fixative, washed in ethanol, and demineralized in buffered formic acid. Plastic embedding of decalcified material was used because of the superior dimensional stability of methacrylate during sample preparation and sectioning. Tissue blocks were dehydrated in increasing alcohol concentrations and embedded. 5 mm thick sections were cut in the coronal plane using a Reichert Polycot microtome. Sections were prepared from midway through the width of the marrow cavity to guard against a sampling bias. Sections for light microscopy were stained using a modified Goldner's trichrome stain, to differentiate bone, osteoid, cartilage, and fibrous tissue.

Sections were cover-slipped using Eukitt's mounting medium (Calibrated Instruments, Ardsley, N.Y.). Histomorphometric analyses were performed under brightfield using a Nikon Optiphot Research microscope. Standard point count stereology techniques using a 10 mm×10 mm eyepiece grid reticular.

Total callus area was measured at 125x magnification as an index of the overall intensity of the healing reaction. Area fractions of bone, cartilage, and fibrous tissue were measured at 250x magnification to examine the relative contribution of each tissue to callus formation. Since the dimensions of the osteotomy gap reflect the baseline (time 0), a measurement of bone area at subsequent time intervals was used to indicate the rate of bone infill. Statistical significance was assessed using analysis of variance, with post-hoc comparisons between groups conducted using Tukey's studentized range test.

In the 5 mm rat osteotomy model described above, it was found that PTH transgene expression can stimulate bone regeneration/repair in live animals. This is a particularly important finding as it is known that hPTH1-34 is a more powerful anabolic agent when given intermittently as opposed to continuously, and it is the continuous-type delivery that results from the gene transfer methods used here.

9. EXAMPLE: DIRECT GENE TRANSFER INTO REGENERATING BONE IN VIVO

Gene activated matrices containing mammalian expression plasmid DNA were implanted into large segmental gaps created in the adult male femur. Implantation of gene-activated matrices containing beta-galactosidase or luciferase plasmids led to DNA uptake and functional enzyme expression by repair cells growing into the gap. Additionally, implantation of a gene activated matrix containing either a bone morphogenetic protein-4 plasmid or a plasmid coding for a fragment of parathyroid hormone (amino acids 1–34) resulting in a biological response of new bone filling the gap. Finally, implantation of a two-plasmid gene-activated matrix encoding bone morphogenetic protein-4 and the parathyroid hormone fragment, which have been shown to act synergistically in vitro, caused new bone to form faster than with either factor alone. These studies demonstrate that for the first time that repair cells in bone can be genetically manipulated in vivo. While serving as a useful tool to study the biology of repair fibroblasts and the wound healing response, the gene activated matrix of the present invention also has wide therapeutic utility.

9.1. MATERIALS AND METHODS

9.1.1. MAMMALIAN HOST MODEL

To create a 5 mm osteotomy, four 1.2 mm diameter pins were screwed into the femoral diaphysis of normal adult Sprague-Dawley rats under general anesthesia and with constant irrigation. A surgical template guided parallel pin placement, which was confirmed by fluorography (pins were set 3.5 mm from the edge of the fixator place and 2.5 mm apart). An external fixator place (30×10×5 mm) was then secured on the pins. External fixator plates were fabricated with aluminum alloy on a CNC mill to ensure high tolerances. Prefabricated fasteners with associated lockwashers and threaded pins were made of stainless steel. All fixator parts were sterilized with ethylene oxide gas prior to surgery. 5 mm segmental defects were created at mid-shaft with a Hall Micro 100 oscillating saw (Zimmer Inc., Warsaw, Ind.). Collagen sponges were placed and held in the osteotomy gap until surrounded by clotted blood; preliminary studies showed that this maneuver fixed the sponge with the osteotomy site. The skin incision was closed with staples. The fixator provided the necessary stability so that the mammalian host's ambulation was unlimited for a several week period.

9.1.2. IMMUNOHISTOCHEMISTRY

Tissues were prepared for light microscopy and immunohistochemistry was performed as described (Wong et al., 1992, J. Biol. Chem. 267: 5592–5598). Histology sections were incubated with a commercially available anti-β-gal antibody (1:200 dilution, 5 Prime→3 Prime) and with a commercially available anti-HA.11 polyclonal antibody (1:500 dilution, BAbCO).

9.1.3. LUCIFERASE AND β-gal ENZYME ASSAYS

Luciferase and β-gal activity was determined using the Luciferase Assay System (Promega) and β-galactosidase Enzyme Assay System (Promega) according to protocols supplied by the manufacturer.

9.1.4. PGAM1 EXPRESSION PLASMID

To assemble pGAM1, mRNA was prepared from day 13.5 p.c. CD-1 mouse embryos using kit reagents and protocols (Poly AT Tract mRNA Isolation System I, Promega). An aliquot of mRNA was used to generate cDNA using commercial reagents (Reverse Transcriptase System, Promega). A full length mouse BMP-4 cDNA coding sequence was generated by the polymerase chain reaction (PCR) using the following conditions: 94° C., 4 min., 1 cycle; 94° C., 1 min., 65° C., 1 min., 72° C., 1 min., 30 cycles; 72° C., 8 min., 1 cycle. The sequence of the PCR primers was based on the known mouse BMP-4 sequence (GenBank): upstream primer-5' CCATGATTCCTGGTAACCGAATGCTG 3'; downstream primer-5' CTCAGCGGCATCCGCACCCCTC 3'. A single PCR product of the expected size (1.3 kb) was purified by agarose gel electrophoresis and cloned into the TA cloning vector (Invitrogen). The 5' end of the BMP-4 insert was further modified (PCR) by addition of a 27 nucleotide sequence that codes for the HA epitope, and the BMP-4 insert was cloned into the pcDNA3 expression vector (InVitrogen). Plasmid DNA was prepared and sequenced (both strands) to ensure the orientation and integrity of the BMP-4 insert.

The pGAM1 plasmid was expressed using an in vitro transcription and translation kit (TNT T7 Coupled Reticulocyte Lysate System, Promega) according to protocols supplied by the manufacturer. Protein radiolabeling, immunoprecipitation, sample preparation and SDS-PAGE, autoradiography, transient transfection, and Western analysis were performed as described (Yin et al., 1995, J. Biol. Chem. 270:10147–10160).

9.1.5. pGAM2 EXPRESSION PLASMID

Human parathyroid hormone cDNA fragments encoding amino acids preprol-34 were generated by PCR. The sequence of the PCR primers was based on known human PTH sequence (GenBank): upstream primer-5' GCGGATC-CGCGATGATACCTGCAAAAGACATG 3'; downstream primer-5' GCGGATCCGCGTCAAAAATTGTGCA-CATCC 3'. This primer pair created BamHI sites at both ends of the PCR fragment. The fragment was digested with BamHI and ligated into a BamHI cloning site in the PLJ retrovirus vector (Wilson et al., 1992, Endocrinol. 130: 2947–2954). A clone with the insert in the coding orientation (pGAM2) eventually was isolated and characterized by DNA sequence analysis.

To generate retroviral stocks, the φ CRIP packaging cell line (Wilson, J. M., et al., 1992, Endocrinology 130:2947–2954) was transfected with 10 μg of recombinant vector DNA using the calcium phosphate method. After an overnight incubation, culture medium (Dulbecco's Modified Eagle's Medium, supplemented with 10% fetal bovine serum, penicillin (100 units/ml), and streptomycin (100 mg/ml) (all reagents from Gibco-BRL Life Technologies, Inc.) containing retrovirion particles was harvested and applied to cultured Rat-1 cells. Independent clones of successfully transduced Rat-1 cells were obtained by standard infection and selection procedures. Briefly, cultured Rat-1 cells were grown to confluence, split 1:10, and selected in G418 (1 mg/ml. Gibco-BRL Life Technologies, Inc.). In some instances, antibiotic-resistant colonies were pooled into a single culture. In other instances, single colonies of resistant cells were maintained. Similar methods were used to generated clones of Rat-1 cells transduced with the BAGT retrovirus, which encodes the bacterial b-gal enzyme.

The hPTH1-34 concentration in cell culture media was estimated using a commercial radioimmunoassay kit (INS-PTH, Nichols) and according to the manufacturer's protocol. The biological activity of the peptide encoded by pGAM2 was evaluated as described (McCauley, et al., 1994, Mol. Cell. Endocrinol. 101: 331–336).

9.1.6. PREPARATION OF GENE ACTIVATED COLLAGEN SPONGES

For each osteotomy gap, lyophilized bovine tracheal collagen (10 mg, Sigma), was thoroughly wetted in a sterile solution of 0.5–1.0 mg plasmid DNA and allowed to incubate for 1–16 hours at 4° C. prior to implantation.

9.1.7. RADIOGRAPHY

Weekly plain film radiographs (posterior-anterior view) were obtained while mammalian hosts were awake using a portable X-ray unit (GE, model 100). The exposure was 1/10 sec at 57 kV and 15 ma.

9.2. RESULTS

9.2.1. OSTEOTOMY MODEL

Our model system employed a 5 mm mid-shaft osteotomy in the adult rat femur. The osteotomy gap was stabilized by a four-pin external fixator. Whereas osteotomy repair in the rat is completed by 9 weeks post-surgery, the manner of repair depends on the size of the gap: a 2 mm gap heals by bony union, but a 5 mm gap heals by fibrous nonunion (Rouleau, J. P., et al., Trans. Ortho. Res. Soc. 20:). Controlled mammalian hosts maintained for up to 13 weeks post-surgery confirmed the observation that 5 mm gaps typically heal by fibrous nonunion. Weekly plain film radiography and histology (FIG. 1A–D) demonstrated that bone did not form in mammalian hosts that received either a 5 mm osteotomy alone (n=3), a 5 mm osteotomy plus a collagen sponge (n=10), or a 5 mm osteotomy plus a collagen sponge containing marker gene naked plasmid DNA (n=23). All 36 control gaps healed by deposition of fibrous tissue. Control femurs exhibited focal periosteal new bone formation (a complication of pin placement). A focal, transient inflammatory response (lymphocytes and macrophages) in gap tissues was also observed post-surgery.

9.2.2. MARKER GENE STUDIES

In a preliminary feasibility study, lacZ and β-gal expression plasmid DNA were successfully transferred in vivo.

The goal was to standardize the gene activated matrix preparation protocol and post-operative time course. A GAM encoding luciferase was placed in the osteotomy gap of one rat and a gene activated matrix encoding β-gal was placed in the gap of a second animal. Three weeks later, gap homogenates (consisting a granulation tissue) were prepared after careful dissection of surrounding bone, cartilage, and skeletal muscle. Aliquots of each homogenate were evaluated for enzyme expression by substrate utilization assay. The expected enzyme activity was detected in each homogenate sample. Positive results were obtained in other experiments in which conditions varied (e.g., DNA dose, time to assay protein expression).

9.2.3. BMP-4 GENE TRANSFER

Having demonstrated that gap cells express functional enzymes following uptake of plasmid DNA from a matrix, we asked whether gene transfer could be used to modulate bone regeneration. We chose to overexpress BMP-4, an osteoinductive factor that normally is expressed by progenitor cells during fracture repair. A full length mouse BMP-4 CDNA was generated by PCR and subcloned into the pcDNA3 (Invitrogen) eukaryotic expression vector (FIG. 2). To specifically detect recombinant proteins, the 3' end of the BMP-4 coding sequence was modified by addition of a hemagglutinin (HA) epitope. Recombinant BMP-4 was expressed from this construct (pGAMI) using an in vitro transcription and translation protocol. Immunoprecipitation studies established the ability of the HA epitope to be recognized by an anti-HA polyclonal antibody. Biosynthesis of recombinant BMP-4 was evaluated following transient transfection of cultured 293T cells with PGAMI plasmid DNA. As demonstrated by immunoprecipitation, BMP-4 molecules were assembled into homodimers, secreted, and processed as expected. Taken together these results established that the HA-epitope was recognized by the anti-HA polyclonal antibody.

Collagen sponges containing pGAMI DNA were placed in the gap of nine adult rats maintained for 4–24 weeks. In one mammalian host sacrificed 4 weeks post surgery, immunohistochemical studies using the anti-HA antibody demonstrated PGAMI expression by repair fibroblasts within the gap. This was significant, given that we did not observe false positive staining in a survey of gap tissue from thirteen control mammalian hosts. Microscopic foci of new bone, originating from both surgical margins, were also observed in the 4 week specimens. Consistent with a classic description of bone formation by autoinduction (Urist, 1965, Science 150:893–999), these foci consisted of bony plates surfaced by large cuboidal osteoblasts and supported by a cellular connective tissue composed of pleomorphic spindled fibroblasts and capillary vessels. In seven mammalian hosts sacrificed 5–12 weeks post-surgery, the amount of radiographic new bone steadily increased (FIG. 3A), even though BMP-4 encoded by the transgene was not detectable by immunohistochemistry. Bridging, defined as new bone extending from the surgical margins across the osteotomy gap, typically was observed by 9 weeks. A ninth mammalian host survived without complication for 24 weeks post-surgery. Sufficient new bone formed by 18 weeks to allow removal of the external fixator, and the mammalian host ambulated well for an additional 6 weeks (FIG. 3D). At sacrifice, the gap was filled with new bone undergoing active remodeling, with the exception of a thin strip of radiolucent tissue near the distal margin of the gap. Given that the mammalian host had successfully ambulated without fixation, this strip was assumed to be partially mineralized. Consistent with this hypothesis biomechanical testing (Frankenburg et al., 1994, Trans. Ortho. Res. Soc. 19:513), which demonstrated that the healed gap had essentially the same mechanical strength as the unoperated femur from the same mammalian host (6.3% difference, maximum torque test). The radiographic appearance of the contralateral (unoperated) femur was unchanged in all nine cases, implying that the effects of gene transfer and BMP-4 overexpression were limited to the osteotomy gap.

9.2.4. TRANSFER AND EXPRESSION OF A PLASMID COCKTAIL (BMP-4+PTH1-34)

Bone regeneration normally is governed by multiple factors acting in a regulated sequence, and we wondered, therefore, if the expression of several anabolic factors would stimulate bone formation more powerfully than a single factor alone. To evaluate this hypothesis, we chose to deliver a two-plasmid GAM encoding BMP-4 plus a peptide fragment of parathyroid hormone (PTH). PTH is an 84 amino acid hormone that raises the plasma and extracellular fluid $Ca^{+2}$ concentration. In skeletal tissues, the intermittent administration of a PTH fragment possessing the structural requirements for biological activity (aa 1–34) produces a true anabolic effect: numerous in vivo and in vitro studies provide strong evidence that PTH1-34 administration in mammalian hosts (including rats) results in uncoupled, high-quality bone formation due to a combined inhibitory effect on osteoclasts and stimulatory effect on osteogenic cells (Dempster et al., 1993, Endocrin Rev. 14:690–709). The PTH1-34 peptide is known to interact synergistically with BMP-4, which up-regulates the expression of functional cell surface PTH receptors in differentiating osteoblasts (Ahrens et al., 1993, J. Bone Min. Res. 12:871–880).

A cDNA fragment encoding human PTH1-34 was generated by PCR. To establish its biological activity, the fragment was subcloned into the PLJ retroviral vector (Wilson et al., 1992, Endocrin, 130:2947–2954), generating the pGAM2 expression plasmid (FIG. 4A). A stock of replication-defective, recombinant retrovirus was prepared and applied to Rat-I cells in culture. Independent clones of transduced Rat-I cells were obtained, and stable integration and expression of retroviral DNA was demonstrated by Southern and Northern analyses. Radioimmunoassay was used to establish the concentration of human PTH 1-34 in conditioned media of individual clones. ROS 17/2.8 cells possess PTH cell surface receptors, which belong to the G protein-coupled receptor superfamily (Dempster et al., 1993, Endocrin. Rev. 14:690–709). Incubation of ROS 17/2.8 cells with aliquots of conditioned media from a stably transduced cell line (secreting >2 pg/ml via radioimmunoassay) resulted in a 2.7-fold increase in CAMP response versus the control, a result that established that the secreted PTH1-34 peptide was biologically active.

GAMs containing pGAM2 plasmid DNA alone stimulated bone (FIG. 4B) GAMs containing the BMP-4 and PTH1-34 expression plasmid DNAs together were then implanted in the osteotomy gap of an additional three mammalian hosts. Bridging was observed by 4 weeks in all three mammalian hosts (one mammalian host was sacrificed at this time for histology), and sufficient new bone had formed by 12 weeks post-implantation in the remaining mammalian hosts to allow removal of the external fixator (FIG. 5). Both mammalian hosts are ambulating well at the time of publication 15 and 26 weeks post-implantation, respectively. Based on plain-film radiography, the effects of gene transfer and overexpression again appeared to be limited to the osteotomy gap.

Subsequent to studies using a collagen sponge, it has also been shown that plasmid DNA could be delivered to cells in a sustained manner following encapsulation within a preparation of block co-polymers of polylactic-polyglycolic particles. The results demonstrate that cultured cells can be transfected by plasmid DNA released from polylactic-polyglycolic particles. Results also indicated that repair fibroblasts (rat osteotomy model) in vivo will take up and express plasmid DNA released from block co-polymers of polylactic-polyglycolic particles. FIG. 7 demonstrates that repair fibroblasts (rat osteotomy model) in vivo will take up and express pGAM2 plasmid DNA following release from polylactic-polyglycolic particles. As shown in FIG. 7, expression of plasmid-encoded PTH1-34 is associated with significant new bone formation in the osteotomy gap.

Taken together, these studies show that the gene activated matrix technology does not depend on a collagenous matrix for success. Therefore, the technology is broad enough that it can be combined with both biological and synthetic matrices.

10. EXAMPLE: TRANSFER OF GENES TO REGENERATING TENDON AND TO REGENERATING CRUCIATE LIGAMENT IN VIVO

There is a clinical need to stimulate scar formation during the repair of Achilles' tendon and ligaments (shoulder and knee) in order to enhance the mechanical competence of the injured tissue. A model system has been developed in which segmental defects in the Achilles' tendon is created and a novel biomaterial, small intestinal submucosa or SIS, is used as a tendon implant/molecular delivery agent. In the present example, the ability to deliver and express marker gene constructs into regenerating tendon tissue using the SIS graft is demonstrated.

10.1. MATERIALS AND METHODS

Segmental defects in Achilles tendon have been created and a preparation of SIS has been used as a tendon implant/molecular delivery system. Plasmid (pSVogal, Promega) stock solutions were prepared according to standard protocols (Sambrook et al., 1989, Molecular Cloning, A Laboratory Manual Cold Spring Harbor Laboratory Press). SIS graft material was prepared from a segment of jejunum of adult pigs (Badylak et al., 1989, J. Surg. Res. 47:74–80). At harvest, mesenteric tissues were removed, the segment was inverted, and the mucosa and superficial submucosa were removed by a mechanical abrasion technique. After returning the segment to its original orientation, the serosa and muscle layers were rinsed, sterilized by treatment with dilute peracetic acid, and stored at 4° C. until use.

Mongrel dogs (all studies) were anesthetized, intubated, placed in right-lateral recumbency upon a heating pad, and maintained with inhalant anesthesia. A lateral incision from the musculotendinous junction to the plantar fascia was used to expose the Achilles, tendon. A double thickness sheet of SIS was wrapped around a central portion of the tendon, both ends were sutured, a 1.5 cm segment of the tendon was removed through a lateral opening in the graft material, and the graft and surgical site were closed. The leg was immobilized for 6 weeks and then used freely for 6 weeks. Graft tissues were harvested at time points indicated below, fixed in Bouins solution, and embedded in paraffin. Tissue sections (8 μm) were cut and used for immunohistochemistry.

10.2. RESULTS

In an initial study, SIS material alone (SIS-alone graft) engrafted and promoted the regeneration of Achilles, tendon following the creation of a segmental defect in mongrel dogs as long as 6 months post surgery. The remodeling process involved the rapid formation of granulation tissue and eventual degradation of the graft. Scar tissue did not form, and evidence of immune-mediated rejection was not observed.

In a second study, SIS was soaked in a plasmid DNA solution (SIS+plasmid graft) and subsequently implanted as an Achilles' tendon graft (n=2 dogs) or a cruciate ligament graft (n=2 dogs) in normal mongrel dogs. A pSVβgal plasmid that employs simian virus 40 regulatory sequences to drive β-galactosidase (β-gal) activity was detectable by immuno-histochemistry using a specific antibody in 4/4 mammalian hosts. As a negative control, β-gal activity was not detected in the unoperated Achilles, tendon and cruciate ligament of these mammalian hosts. It appeared, therefore, that SIS facilitated the uptake and subsequent expression of plasmid DNA by neotendon cells in both tendon and ligament.

A third study was designed to evaluate the time course of β-gal transgene expression. SIS+plasmid grafts were implanted for 3, 6, 9, and 12 weeks (n=2 dogs per time point) and transgene expression was assayed by immunohistochemistry. Cross-sections (8 μm) of Bouins fixed, paraffin embedded tissue were cut and mounted on Probeon Plus slides (Fisher). Immunohisto-chemistry was performed according to the protocol provided with the Histostain-SP kit (Zymed). In brief, slides were incubated with a well characterized anti-β-galactosidase antibody (12:00 dilution, 5 Prime→3 Prime), washed in PBS, incubated with a biotinylated second antibody, washed, stained with the enzyme conjugate plus a substrate-chromogen mixture, and then counterstained with hematoxylin and eosin.

Bacterial β-gal activity was detected in tendons that received the SIS+plasmid graft (8/8 mammalian hosts). Although not rigorously quantitative, transgene expression appeared to peak at 9–12 weeks. Bacterial β-gal gene expression was not detected in 35 mammalian hosts that received SIS-alone grafts.

11. EXAMPLE: ADENOVIRAL GENE TRANSFER INTO REGENERATING BONE IN VIVO

An alternative method to achieve in vivo gene transfer into regenerating tissue is to utilize an adenovirus-mediated transfer event. Successful adenoviral gene transfer of a marker gene construct into bone repair cells in the rat osteotomy model has been achieved.

11.1. MATERIALS AND METHODS

Adenoviral vector pAd. CMVlacZ, is an example of a replication-defective adenoviral vector which can replicate in permissive cells (Stratford-Perricaudet et al., 1992, J. Clin. Invest. 90:626–630). In this particular vector the early enhancer/promoter of the cytomegalovirus (CMV) is used to drive transcription of lacZ with an SV40 polyadenylation sequence cloned downstream from the reporter gene (Davidson et al., 1993, Nature Genetics 3:219–223).

pAd.RSV4 has essentially the same backbone as pAdCMVlacZ, however the CMV promoter and the single BglII cloning site has been replaced in a cassette-like fashion with a BglII fragment that consists of an RSV promoter, a multiple cloning site, and a poly($A^+$) site. The greater flexibility of this vector is contemplated to be useful in subcloning osteotropic genes, such as the hPTH1-34 cDNA fragment, for use in further studies.

An Ultra Fiber™ implant was soaked for 6 minutes in a solution of AdCMV lacZ virus ($10^{10}$–$10^{11}$ plaque forming units or PFU/ml) and then implanted into the osteotomy site. The defect was allowed to heal for 3 weeks, during which time the progress of the wound healing response was monitored by weekly radiographic examination. By three weeks, it was estimated that 40% of the defect was filled with callus tissue. The mammalian host was sacrificed and tissues were fixed in Bouins fixation and then demineralized for 7 days using standard formic acid solutions.

11.2. RESULTS

The results obtained conclusively demonstrated expression of the marker gene product in chondrocyte-like cells of the osteotomy gap (FIG. 6). The nuclear-targeted signal has also been observed in pre-osteoblasts.

12. EXAMPLE: TRANSFER OF GENES TO SKELETAL MUSCLE

There is a clinical need to stimulate scar formation during the repair of soft tissues besides Achilles' tendon and ligaments (shoulder and knee) in order to enhance the mechanical competence of the injured tissue. A model system has been developed in which incisions in adult rat skeletal muscle are made and a suture preparation coated with a preparation of sustained release PLGA particles and plasmid DNA is used as a skeletal muscle/gene delivery device. To demonstrate the feasibility of the coating compositions and methods of the invention, a surgical suture was coated with marker DNA (encoding human placental alkaline phosphatase) and used to suture rat muscle tissue. The experiment demonstrates successful transfer and expression of DNA in the tissue repaired with the coated suture.

12.1 MATERIALS AND METHODS

12.1.1 PREPARATION OF DNA-PLGA COATING COMPOSITION

To 1.5 mL of a PLGA/chloroform solution (3% (w/v) 50/50 polylactic polyglycolic acid PLGA co-polymer, ave. MW 90,000, inherent viscosity 1.07) was added 0.2 mL of a solution containing marker DNA encoding human placental alkaline phosphatase (1 mg DNA, 0.5 mM Tris-EDTA, 0.5 mM EDTA, pH 7.3). The solution was emulsified by vortexing for 2 minutes followed by sonicating for 30 seconds at about 0° C. using a microtip probe-type sonicator at 55 Watts output. This process yielded an emulsion that looked very milky.

12.1.2 COATING A SURGICAL SUTURE

A hole was pierced in a piece of Teflon-coated foil (Norton Performance Plastic Corp., Akron, Ohio) using a 22-gauge needle. On the hole was placed a drop (about 60 μL) of the DNA-PLGA emulsion. A 70 cm length of 3-0 chromic suture (Ethicon) was drawn through the hole to coat the suture. As the suture passed through the hole it became coated with a thin (ca. 30 μm-thick), uniform coating of the coating composition. The suture was allowed to air dry for about 3 minutes, and the coating process repeated 15 times, allowing each coat to air dry. The coated suture was examined by electron microscopy (150X) and the suture was found to be coated with a uniform coating of DNA-PLGA. Furthermore, the coating remained intact even after passing the suture through tissue multiple times.

12.1.3 REPAIRING SKELETAL MUSCLE WITH THE COATED SUTURE

The suture prepared above was sewn into the skeletal muscle tissue of two normal adult rats with satisfactory surgical results. The suture exhibited good tie-down properties. One week later, muscle plus suture was dissected, snap frozen in liquid nitrogen and ground into a powder. The powder was incubated in 200 μL lysis buffer, exposed to three freeze-thaw cycles and clarified. The clear liquid was assayed for alkaline phosphatase activity using standard methods after incubation at 65° C.

12.2 RESULTS

The results indicated that rat skeletal muscle sewn with coated sutures and retrieved after one week exhibited alkaline phosphatase activity, signifying that the marker alkaline phosphatase gene was expressed in the muscle tissue. Control retrievals showed no significant alkaline phosphatase activity. These data demonstrate that emulsions can be used to effectively coat sutures and deliver genes to proliferating repair cells in vivo.

13. EXAMPLE: TRANSFER OF GENES TO BLOOD VESSEL

There is a clinical need to prevent excessive fibrosis (restenosis), as, for example, may occur during blood vessel repair following angioplasty. This might be accomplished, for example, by delivery of genes that code for lysyl oxidase inhibitors, or by transfer of genes that code for certain TGF-βs. There is, in addition, a clinical need to regulate angiogenesis, as, for example, in vascular insufficiency disorders, where the goal would be to stimulate new vessel formation in order to prevent tissue hypoxia and cell death. A model system has been developed in which repair cells in large blood vessels in rabbit are transfected with a preparation of sustained release PLGA particles and plasmid DNA. Repair cells are present because these rabbit blood vessels harbor a foam cell lesion that mimics clinical atherosclerosis in humans. The present example demonstrates the ability to deliver and express marker gene constructs into large blood vessel repair cells.

13.1. MATERIALS AND METHODS

New Zealand white rabbits of either sex, weighing 3.1 to 3.5 kg, were used for this study. Rabbits were anesthetized using Ketamine (35/mg/Kg) and Xylazine (5 mg/kg) given intramuscularly, and maintenance anesthesia was achieved with intravenous ketamine (8 mg/kg) administered via a marginal vein. Approximately 2 cm Segments of both iliac arteries between the descending aortic bifurcation and inguinal ligament were isolated, tied off proximally, and all small branches of this arterial segments were ligated. Local thrombus were prevented by the ear-marginal vein administration of heparin (100 mg). Via an iliac arteriotomy, a balloon angioplasty catheter (2.0 mm balloon) was introduced into iliac arteric segments and balloon was dilated for 1-minute at 8 atm pressure.

Following balloon dilatation, the angioplasty catheter was removed, 20 mg of heparin was injected intra-arterially to prevent distal thrombosis. Both ends of iliac artery were tightened with 10.0 silk, the 5 mg/ml DNA-Nanoparticle suspension was infused in each iliac artery over 3 minutes at 0.5 atm. The wound was sutured. Rabbits were sacrificed 2 weeks after the balloon angioplasty and nanoparticle delivery. Through a vertical lower abdominal incision, both iliac arteries were isolated. A 2 cm segment of iliac artery was excised bilaterally. Carotid arteries from rabbit was taken as a control sample. The tissue was preserved in liquid nitrogen for alkaline phosphatase assay.

13.2. RESULTS

The results of the phosphatase expression assays indicated that a nanoparticle plus DNA formulation was capable of delivering nucleic acids to repair cells in the iliac arterics of adult rabbits injured with a ballon catheter. Both the right and left iliac arterics were positive for phosphatase activity after exposure to nanoparticle plus DNA formulations. No phosphatase activity was detected in the control aorta. These positive results indicate upon exposure to a gene activated matrix repair cells in large blood vessels can take up and express nucleic acid molecules.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A method for transferring a DNA molecule that directs the expression of a gene product into a mammalian repair cell, comprising applying a biocompatible matrix containing the DNA molecule to a wound in a mammalian subject, so that repair cells at the wound site acquire the DNA molecule, and express the gene product in vivo.

2. The method of claim 1 wherein the biocompatible matrix is collagenous, metal, hydroxyapatite, bioglass, aluminate, bioceramic materials, purified proteins or extracellular matrix compositions.

3. The method of claim 1 wherein the biocompatible matrix is collagen.

4. The method of claim 3 wherein the collagen is type II collagen.

5. The method of claim 1 wherein the DNA molecule encodes a therapeutic protein.

6. The method of claim 1 wherein the DNA molecule encodes a growth factor.

7. The method of claim 1 wherein the DNA molecule is more than one DNA molecule.

8. The method of claim 6 wherein the growth factor is transforming growth factor-βeta (TGF-β), fibroblast growth factor (FGF), platelet derived growth factor (PDGF), insulin like growth factor (IGF), or bone morphogenic factor (BMP).

9. The method of claim 5 wherein the therapeutic protein is a hormone.

10. The method of claim 9 wherein the hormone is growth hormone (GH).

11. The method of claim 9 wherein the hormone is human parathyroid hormone (PTH).

12. The method of claim 1, wherein said wound site is a site of connective tissue injury.

13. The method of claim 1, wherein said wound site is a site of organ damage.

14. A method for transferring a DNA molecule that directs the expression of a gene product into a mammalian repair cell, comprising applying a biocompatible matrix containing the DNA molecule to a wound in a mammalian subject, wherein said matrix is sufficient to allow infiltration of repair cells, so that repair cells at the wound site acquire the DNA molecule, and express the gene product in vivo.

* * * * *